United States Patent [19]

de Haan

[11] Patent Number: 5,919,705
[45] Date of Patent: Jul. 6, 1999

[54] PLANT VIRUS DNA CONSTRUCTS AND VIRUS RESISTANT PLANTS COMPRISING SAID CONSTRUCTS

[75] Inventor: Petrus Theodorus de Haan, Enkhuizen, Netherlands

[73] Assignee: Novartis Finance Corporation, New York, N.Y.

[21] Appl. No.: 08/553,619

[22] PCT Filed: Jun. 3, 1994

[86] PCT No.: PCT/EP94/01817

§ 371 Date: Dec. 1, 1995

§ 102(e) Date: Dec. 1, 1995

[87] PCT Pub. No.: WO94/29464

PCT Pub. Date: Dec. 22, 1994

[30] Foreign Application Priority Data

Jun. 4, 1993 [GB] United Kingdom .................. 9311593

[51] Int. Cl.$^6$ .............................. A01H 4/00; C12N 5/14; C07H 21/00
[52] U.S. Cl. ........................ 435/418; 435/69.1; 435/69.7; 435/419; 536/23.1; 536/23.72; 536/24.1; 800/278; 800/279; 800/288; 800/301
[58] Field of Search ..................... 800/578, 279, 800/288, 301; 435/69.1, 69.7, 418, 419; 536/23.72, 23.1, 24.1

[56] References Cited

U.S. PATENT DOCUMENTS 5,614,395  3/1997  Ryals et al. .......................... 435/172.3

OTHER PUBLICATIONS

Nejidat et al. Physiologia Plantarium, vol. 80 pp. 662–668, 1990.

*Primary Examiner*—Jeffrey Stucker
*Assistant Examiner*—Phuong T. Bui
*Attorney, Agent, or Firm*—Thomas Hoxie; J. Timothy Meigs

[57] ABSTRACT

DNA constructs encoding an RNA molecule capable of interacting with an RNA dependent RNA polymerase encoded for by a virus when invading a plant such that either an eliciting element or a plus sense RNA is produced as a consequence of the interaction with the RNA dependent RNA polymerase encoded by the said invading virus, whereby any produced plus sense RNA molecule is capable of encoding for an eliciting element, plants containing such constructs and processes for obtaining such plants.

26 Claims, 3 Drawing Sheets

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
       (A) LENGTH: 1860 base pairs
       (B) TYPE: nucleic acid
       (C) STRANDEDNESS: single
       (D) TOPOLOGY: unknown (vi) ORIGINAL SOURCE:
       (A) ORGANISM: Chimaeric cucumber mosaic virus RNA 3

(ix) FEATURE:
       (A) NAME/KEY: CDS
       (B) LOCATION: 123..599

(ix) FEATURE:

```
ATATAGAGAG TGTGTGTGCT GTGTTTTCTC TTTTGTGTCG TAGAATTGAG TCGAGTC        896

ATG GAC AAA TCT GAA TCA ACC AGT GCT GGT CGT AAC CGT CGA CGT CGT       944
Met Asp Lys Ser Glu Ser Thr Ser Ala Gly Arg Asn Arg Arg Arg Arg
  1               5                  10                  15

CCG CGT CGT GGT TCC CGC TCC GCC CCC TCC TCC GCG GAT GCT AAC TTT       992
Pro Arg Arg Gly Ser Arg Ser Ala Pro Ser Ser Ala Asp Ala Asn Phe
             20                  25                  30

AGA GTC TTG TCG CAG CAG CTT TCG CGA CTT AAT AAG ACG TTA GCA GCT      1040
Arg Val Leu Ser Gln Gln Leu Ser Arg Leu Asn Lys Thr Leu Ala Ala
         35                  40                  45

GGT CGT CCA ACT ATT AAC CAC CCA ACC TTT GTA GGG AGT GAA CGC TGT      1088
Gly Arg Pro Thr Ile Asn His Pro Thr Phe Val Gly Ser Glu Arg Cys
     50                  55                  60

AAA CCT GGG TAC ACG TTC ACA TCT ATT ACC CTA AAG CCA CCA AAA ATA      1136
Lys Pro Gly Tyr Thr Phe Thr Ser Ile Thr Leu Lys Pro Pro Lys Ile
 65                  70                  75                  80

GAC CGT GGG TCT TAT TAC GGT AAA AGG TTG TTA TTA CCT GAT TCA GTC      1184
Asp Arg Gly Ser Tyr Tyr Gly Lys Arg Leu Leu Leu Pro Asp Ser Val
                 85                  90                  95

ACG GAA TAT GAT AAG AAA CTT GTT TCG CGC ATT CAA ATT CGA GTT AAT      1232
Thr Glu Tyr Asp Lys Lys Leu Val Ser Arg Ile Gln Ile Arg Val Asn
             100                 105                 110

CCT TTG CCG AAA TTC GAT TCT ACC GTG TGG GTG ACA GTC CGT AAA GTT      1280
Pro Leu Pro Lys Phe Asp Ser Thr Val Trp Val Thr Val Arg Lys Val
         115                 120                 125

CCT GCC TCC TCG GAC TTA TCC GTT GCC GCC ATC TCT GCT ATG TTT GCG      1328
Pro Ala Ser Ser Asp Leu Ser Val Ala Ala Ile Ser Ala Met Phe Ala
     130                 135                 140

GAC GCC GCA TTT GGA GTC CAA GCT AAC AAC AAA TTG TTG TAT GAT CTT      1376
Asp Ala Ala Phe Gly Val Gln Ala Asn Asn Lys Leu Leu Tyr Asp Leu
145                 150                 155                 160

TCG GCG GGA GCC TCA CCG GTA CTG GTT TAT CAG TAC ATG CGC GCT GAT      1424
Ser Ala Gly Ala Ser Pro Val Leu Val Tyr Gln Tyr Met Arg Ala Asp
             165                 170                 175

ATA GGT GAC ATG AGA AAG TAC GCC GTC CTC GTG TAT TCA AAA GAC GAT      1472
Ile Gly Asp Met Arg Lys Tyr Ala Val Leu Val Tyr Ser Lys Asp Asp
         180                 185                 190

GCG CTC GAG ACG GAC GAG CTA GTA CTT CAT GTT GAC ATC GAG CAC CAA      1520
Ala Leu Glu Thr Asp Glu Leu Val Leu His Val Asp Ile Glu His Gln
     195                 200                 205

CGC ATT CCC ACA TCT AGA GTA CTC CCA GTC TGATTCCGTG TTCCCAGAAC        1570
Arg Ile Pro Thr Ser Arg Val Leu Pro Val
         210                 215

CCTCCCTCCG ATTTCTGTGG CGGGAGCTGA GTTGGCAGTT CTGCTATAAA CTGTCTGAAG   1630

TCACTAAACG TTTTACGGTG AACGGGTTGT CCATCCAGCT TACGGCTAAA ATGGTCAGTC   1690

GTGGAGAAAT CCACGCCAGC AGATTTACAA ATCTCTGAGG CGCCTTTGAA ACCATCTCCT   1750

AGGTTTTTTC GGAAGGACTT CGGTCCGTGT ACCTCTAGCA CAACGTGCTA GTCTTAGGGT   1810

ACGGGTGCCC CTTGTCTTCG CACCTTCGTG GGGGCTCCAA AAGGAGACCA              1860

(2) INFORMATION FOR SEQ ID NO:2:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO:2:
```

```
Met Ala Tyr Ser Ile Thr Ser Pro Ser Gln Phe Val Phe Leu Ser Ser
 1               5                  10                  15

Val Trp Ala Asp Pro Ile Glu Leu Leu Asn Val Cys Thr Asn Ser Leu
            20                  25                  30

Gly Asn Gln Phe Gln Thr Gln Gln Ala Arg Thr Thr Val Gln Gln Gln
        35                  40                  45

Phe Ser Glu Val Trp Lys Pro Phe Pro Gln Ser Thr Val Arg Phe Pro
    50                  55                  60

Gly Asp Val Tyr Lys Val Tyr Arg Tyr Asn Ala Val Leu Asp Pro Leu
 65                  70                  75                  80

Ile Thr Ala Leu Leu Gly Ser Phe Asp Thr Arg Asn Arg Ile Ile Glu
                85                  90                  95

Val Glu Asn Gln Gln Asn Pro Thr Thr Ala Glu Thr Leu Asp Ala Thr
                100                 105                 110

Arg Arg Val Asp Asp Ala Thr Val Ala Ile Arg Ser Ala Ile Asn Asn
            115                 120                 125

Leu Val Asn Glu Leu Val Arg Gly Thr Gly Leu Tyr Asn Gln Asn Thr
130                 135                 140

Phe Glu Ser Met Ser Gly Leu Val Trp Thr Ser Ala Pro Ala Ser
145                 150                 155
```

(2) INFORMATION FOR SEQ ID NO:3:

(i) SEQUENCE CHARACTERISTICS:
        (A) LENGTH: 218 amino acids
        (B) TYPE: amino acid
        (D) TOPOLOGY: linear (ii) MOLECULE TYPE: protein (xi) SEQUENCE DESCRIPTION: SEQ ID NO:3:

```
Met Asp Lys Ser Glu Ser Thr Ser Ala Gly Arg Asn Arg Arg Arg Arg
 1               5                  10                  15

Pro Arg Arg Gly Ser Arg Ser Ala Pro Ser Ser Ala Asp Ala Asn Phe
            20                  25                  30

Arg Val Leu Ser Gln Gln Leu Ser Arg Leu Asn Lys Thr Leu Ala Ala
        35                  40                  45

Gly Arg Pro Thr Ile Asn His Pro Thr Phe Val Gly Ser Glu Arg Cys
    50                  55                  60

Lys Pro Gly Tyr Thr Phe Thr Ser Ile Thr Leu Lys Pro Pro Lys Ile
 65                  70                  75                  80

Asp Arg Gly Ser Tyr Tyr Gly Lys Arg Leu Leu Leu Pro Asp Ser Val
                85                  90                  95

Thr Glu Tyr Asp Lys Lys Leu Val Ser Arg Ile Gln Ile Arg Val Asn
                100                 105                 110

Pro Leu Pro Lys Phe Asp Ser Thr Val Trp Val Thr Val Arg Lys Val
            115                 120                 125

Pro Ala Ser Ser Asp Leu Ser Val Ala Ala Ile Ser Ala Met Phe Ala
        130                 135                 140

Asp Ala Ala Phe Gly Val Gln Ala Asn Asn Lys Leu Leu Tyr Asp Leu
145                 150                 155                 160

Ser Ala Gly Ala Ser Pro Val Leu Val Tyr Gln Tyr Met Arg Ala Asp
                165                 170                 175

Ile Gly Asp Met Arg Lys Tyr Ala Val Leu Val Tyr Ser Lys Asp Asp
                180                 185                 190

Ala Leu Glu Thr Asp Glu Leu Val Leu His Val Asp Ile Glu His Gln
```

```
                    195                 200                 205
Arg Ile Pro Thr Ser Arg Val Leu Pro Val
    210                 215

(2) INFORMATION FOR SEQ ID NO:4:

(i) SEQUENCE CHARACTERISTICS:
        (A) LENGTH: 1696 base pairs
        (B) TYPE: nucleic acid
        (C) STRANDEDNESS: single
        (D) TOPOLOGY: unknown (vi) ORIGINAL SOURCE:
        (A) ORGANISM: Chimaeric cucumber mosaic virus RNA 3

(ix) FEATURE:
        (A) NAME/KEY: CDS
        (B) LOCATION: 123..437

(xi) SEQUENCE DESCRIPTION: SEQ ID NO:4:

GTAATCTTAC CACTCGTGTG TGTGCGTGTG TGTGTGTCGA GTCGTGTTGT CCGCACATTT       60

GAGTCGTGCT GTCCGCACAT ATATTTTACC TTTTGTGTAC AGTGTGTTAG ATTTCCCGAG      120

CC ATG GCA TGC GAC TAC ACT TGC GGT TCT AAC TGC TAC TCT TCT TCA        167
   Met Ala Cys Asp Tyr Thr Cys Gly Ser Asn Cys Tyr Ser Ser Ser
   1               5                  10                  15

GAC GTT TCT ACT GCT CAA GCT GCC GGA TAT AAA CTT CAC GAA GAC GGT        215
Asp Val Ser Thr Ala Gln Ala Ala Gly Tyr Lys Leu His Glu Asp Gly
                20                  25                  30

GAA ACT GTT GGA TCT AAT TCT TAC CCA CAC AAA TAC AAC AAC TAC GAA        263
Glu Thr Val Gly Ser Asn Ser Tyr Pro His Lys Tyr Asn Asn Tyr Glu
            35                  40                  45

GGT TTT GAT TTC TCT GTG AGC TCT CCC TAC TAC GAA TGG CCT ATC CTC        311
Gly Phe Asp Phe Ser Val Ser Ser Pro Tyr Tyr Glu Trp Pro Ile Leu
        50                  55                  60

TCT AGC GGT GAT GTT TAC TCT GGT GGT TCT CCA GGT GCT GAC CGT GTC        359
Ser Ser Gly Asp Val Tyr Ser Gly Gly Ser Pro Gly Ala Asp Arg Val
    65                  70                  75

GTC TTC AAC GAA AAC AAC CAA CTA GCT GGT GTT ATC ACT CAC ACT GGT        407
Val Phe Asn Glu Asn Asn Gln Leu Ala Gly Val Ile Thr His Thr Gly
80                  85                  90                  95

GCT TCT GGT AAC AAC TTC GTT GAA TGT ACA TAACCATGGT GTATTAGTAT         457
Ala Ser Gly Asn Asn Phe Val Glu Cys Thr
                100                 105

ATAAGTATTG TGAGTCTGTA CATAATACTA TATCTATAGT GTCCTGTGTG AGTTGATACA      517

GTAGACATCT GTGACGCGAT GCCGTGTTGA GAAGGGAACA CATCTGGTTT TAGTAAGCCT      577

ACATCACAGT TTTGAGGTTC AATTCCTCAT ACTCCCTGTT GAGTCCCTTA CTTTCTCATG      637

GATGCTTCTC CGCGAGATTG CGTTATTGTC TACTGACTAT ATAGAGAGTG TGTGTGCTGT      697

GTTTTCTCTT TTGTGTCGTA GAATTGAGTC GAGTCATGGA CAAATCTGAA TCAACCAGTG      757

CTGGTCGTAA CCGTCGACGT CGTCCGCGTC GTGGTTCCCG CTCCGCCCCC TCCTCCGCGG      817

ATGCTAACTT TAGAGTCTTG TCGCAGCAGC TTTCGCGACT TAATAAGACG TTAGCAGCTG      877

GTCGTCCAAC TATTAACCAC CCAACCTTTG TAGGGAGTGA ACGCTGTAAA CCTGGGTACA      937

CGTTCACATC TATTACCCTA AAGCCACCAA AAATAGACCG TGGGTCTTAT TACGGTAAAA      997

GGTTGTTATT ACCTGATTCA GTCACGGAAT ATGATAAGAA ACTTGTTTCG CGCATTCAAA     1057

TTCGAGTTAA TCCTTTGCCG AAATTCGATT CTACCGTGTG GGTGACAGTC CGTAAAGTTC     1117

CTGCCTCCTC GGACTTATCC GTTGCCGCCA TCTCTGCTAT GTTTGCGGAC GGAGCCTCAC     1177

CGGTACTGGT TTATCAGTAC GCCGCATTTG GAGTCCAAGC TAACAACAAA TTGTTGTATG     1237
```

```
ATCTTTCGGC GATGCGCGCT GATATAGGTG ACATGAGAAA GTACGCCGTC CTCGTGTATT    1297

CAAAAGACGA TGCGCTCGAG ACGGACGAGC TAGTACTTCA TGTTGACATC GAGCACCAAC    1357

GCATTCCCAC ATCTAGAGTA CTCCCAGTCT GATTCCGTGT TCCCAGAACC CTCCCTCCGA    1417

TTTCTGTGGC GGGAGCTGAG TTGGCAGTTC TGCTATAAAC TGTCTGAAGT CACTAAACGT    1477

TTTACGGTGA ACGGGTTGTC CATCCAGCTT ACGGCTAAAA TGGTCAGTCG TGGAGAAATC    1537

CACGCCAGCA GATTTACAAA TCTCTGAGGC GCCTTTGAAA CCATCTCCTA GGTTTTTTCG    1597

GAAGGACTTC GGTCCGTGTA CCTCTAGCAC AACGTGCTAG TCTTAGGGTA CGGGTGCCCC    1657

TTGTCTTCGC ACCTTCGTGG GGGCTCCAAA AGGAGACCA                            1696
```

(2) INFORMATION FOR SEQ ID NO:5:

(i) SEQUENCE CHARACTERISTICS:
        (A) LENGTH: 105 amino acids
        (B) TYPE: amino acid
        (D) TOPOLOGY: linear (ii) MOLECULE TYPE: protein (xi) SEQUENCE DESCRIPTION: SEQ ID NO:5:

```
Met Ala Cys Asp Tyr Thr Cys Gly Ser Asn Cys Tyr Ser Ser Asp
 1               5                  10                  15

Val Ser Thr Ala Gln Ala Ala Gly Tyr Lys Leu His Glu Asp Gly Glu
                20                  25                  30

Thr Val Gly Ser Asn Ser Tyr Pro His Lys Tyr Asn Asn Tyr Glu Gly
            35                  40                  45

Phe Asp Phe Ser Val Ser Ser Pro Tyr Tyr Glu Trp Pro Ile Leu Ser
        50                  55                  60

Ser Gly Asp Val Tyr Ser Gly Gly Ser Pro Gly Ala Asp Arg Val Val
 65                 70                  75                  80

Phe Asn Glu Asn Asn Gln Leu Ala Gly Val Ile Thr His Thr Gly Ala
                85                  90                  95

Ser Gly Asn Asn Phe Val Glu Cys Thr
               100                 105
```

(2) INFORMATION FOR SEQ ID NO:6:

(i) SEQUENCE CHARACTERISTICS:
        (A) LENGTH: 2173 base pairs
        (B) TYPE: nucleic acid
        (C) STRANDEDNESS: single
        (D) TOPOLOGY: unknown (vi) ORIGINAL SOURCE:
        (A) ORGANISM: Chimaeric cucumber mosaic virus RNA 3

(ix) FEATURE:
        (A) NAME/KEY: CDS
        (B) LOCATION: 123..914

(xi) SEQUENCE DESCRIPTION: SEQ ID NO:6:

```
GTAATCTTAC CACTCGTGTG TGTGCGTGTG TGTGTGTCGA GTCGTGTTGT CCGCACATTT      60

GAGTCGTGCT GTCCGCACAT ATATTTTACC TTTTGTGTAC AGTGTGTTAG ATTTCCCGAG     120

CC ATG GCT CTA GTT GTT AAA GGT AAG GTA AAT ATT AAT GAG TTT ATC        167
   Met Ala Leu Val Val Lys Gly Lys Val Asn Ile Asn Glu Phe Ile
    1               5                  10                  15

GAT CTG TCA AAG TCT GAG AAA CTT CTC CCG TCG ATG TTC ACG CCT GTA       215
Asp Leu Ser Lys Ser Glu Lys Leu Leu Pro Ser Met Phe Thr Pro Val
                20                  25                  30
```

| | | |
|---|---|---|
| AAG AGT GTT ATG GTT TCA AAG GTT GAT AAG ATT ATG GTC CAT GAA AAT<br>Lys Ser Val Met Val Ser Lys Val Asp Lys Ile Met Val His Glu Asn<br>              35                     40                   45 | 263 |
| GAA TCA TTG TCT GAA GTA AAT CTC TTA AAA GGT GTA AAA CTT ATA GAA<br>Glu Ser Leu Ser Glu Val Asn Leu Leu Lys Gly Val Lys Leu Ile Glu<br>        50                     55                    60 | 311 |
| GGT GGG TAT GTT TGC TTA GTT GGT CTT GTT GTG TCC GGT GAG TGG AAT<br>Gly Gly Tyr Val Cys Leu Val Gly Leu Val Val Ser Gly Glu Trp Asn<br>       65                   70                   75 | 359 |
| TTC CCA GAT AAT CGC CGT GGT GGT GTG AGT GTC TGC ATG GTT GAC AAG<br>Phe Pro Asp Asn Arg Arg Gly Gly Val Ser Val Cys Met Val Asp Lys<br>80                   85                    90                 95 | 407 |
| AGA ATG GAA AGA GCG GAC GAA GCC ACA CTG GGG TCA TAT TAC ACT GCT<br>Arg Met Glu Arg Ala Asp Glu Ala Thr Leu Gly Ser Tyr Tyr Thr Ala<br>             100                    105                110 | 455 |
| GCT GCT AAA AAG CGG TTT CAG TTT AAA GTG GTC CCA AAT TAC GGT ATT<br>Ala Ala Lys Lys Arg Phe Gln Phe Lys Val Val Pro Asn Tyr Gly Ile<br>             115                    120                125 | 503 |
| ACA ACA AAG GAT GCA GAA AAG AAC ATA TGG CAG GTC TTA GTA AAT ATT<br>Thr Thr Lys Asp Ala Glu Lys Asn Ile Trp Gln Val Leu Val Asn Ile<br>        130                    135                   140 | 551 |
| AAA AAT GTA AAA ATG AGT GCG GGC TAC TGC CCT TTG TCA TTA GAA TTT<br>Lys Asn Val Lys Met Ser Ala Gly Tyr Cys Pro Leu Ser Leu Glu Phe<br>145                   150                    155 | 599 |
| GTG TCT GTG TGT ATT GTT TAT AAA AAT AAT ATA AAA TTG GGT TTG AGG<br>Val Ser Val Cys Ile Val Tyr Lys Asn Asn Ile Lys Leu Gly Leu Arg<br>160                   165                    170                175 | 647 |
| GAG AAA GTA ACG AGT GTG AAC GAT GGA GGA CCC ATG GAA CTT TCG GAA<br>Glu Lys Val Thr Ser Val Asn Asp Gly Gly Pro Met Glu Leu Ser Glu<br>             180                    185                190 | 695 |
| GAA GTT GTT GAT GAG TTC ATG GAG AAT GTT CCA ATG TCG GTT AGA CTC<br>Glu Val Val Asp Glu Phe Met Glu Asn Val Pro Met Ser Val Arg Leu<br>             195                    200                205 | 743 |
| GCA AAG TTT CGA ACC AAA TCC TCA AAA AGA GGT CCG AAA AAT AAT AAT<br>Ala Lys Phe Arg Thr Lys Ser Ser Lys Arg Gly Pro Lys Asn Asn Asn<br>        210                    215                   220 | 791 |
| AAT TTA GGT AAG GGG CGT TCA GGC GGA AGG CCT AAA CCA AAA AGT TTT<br>Asn Leu Gly Lys Gly Arg Ser Gly Gly Arg Pro Lys Pro Lys Ser Phe<br>225                   230                    235 | 839 |
| GAT GAA GTT GAA AAA GAG TTT GAT AAT TTG ATT GAA GAT GAA GCC GAG<br>Asp Glu Val Glu Lys Glu Phe Asp Asn Leu Ile Glu Asp Glu Ala Glu<br>240                   245                    250               255 | 887 |
| ACG TCG GTC GCG GAT TCT GAT TCG TAT TAACCATGGT GTATTAGTAT<br>Thr Ser Val Ala Asp Ser Asp Ser Tyr<br>             260 | 934 |
| ATAAGTATTG TGAGTCTGTA CATAATACTA TATCTATAGT GTCCTGTGTG AGTTGATACA | 994 |
| GTAGACATCT GTGACGCGAT GCCGTGTTGA GAAGGGAACA CATCTGGTTT TAGTAAGCCT | 1054 |
| ACATCACAGT TTTGAGGTTC AATTCCTCAT ACTCCCTGTT GAGTCCCTTA CTTTCTCATG | 1114 |
| GATGCTTCTC CGCGAGATTG CGTTATTGTC TACTGACTAT ATAGAGAGTG TGTGTGCTGT | 1174 |
| GTTTTCTCTT TTGTGTCGTA GAATTGAGTC GAGTCATGGA CAAATCTGAA TCAACCAGTG | 1234 |
| CTGGTCGTAA CCGTCGACGT CGTCCGCGTC GTGGTTCCCG CTCCGCCCCC TCCTCCGCGG | 1294 |
| ATGCTAACTT TAGAGTCTTG TCGCAGCAGC TTTCGCGACT TAATAAGACG TTAGCAGCTG | 1354 |
| GTCGTCCAAC TATTAACCAC CCAACCTTTG TAGGGAGTGA ACGCTGTAAA CCTGGGTACA | 1414 |
| CGTTCACATC TATTACCCTA AAGCCACCAA AAATAGACCG TGGGTCTTAT TACGGTAAAA | 1474 |
| GGTTGTTATT ACCTGATTCA GTCACGGAAT ATGATAAGAA ACTTGTTTCG CGCATTCAAA | 1534 |

-continued

```
TTCGAGTTAA TCCTTTGCCG AAATTCGATT CTACCGTGTG GGTGACAGTC CGTAAAGTTC    1594

CTGCCTCCTC GGACTTATCC GTTGCCGCCA TCTCTGCTAT GTTTGCGGAC GCCGCATTTG    1654

GAGTCCAAGC TAACAACAAA TTGTTGTATG ATCTTTCGGC GGGAGCCTCA CCGGTACTGG    1714

TTTATCAGTA CATGCGCGCT GATATAGGTG ACATGAGAAA GTACGCCGTC CTCGTGTATT    1774

CAAAAGACGA TGCGCTCGAG ACGGACGAGC TAGTACTTCA TGTTGACATC GAGCACCAAC    1834

GCATTCCCAC ATCTAGAGTA CTCCCAGTCT GATTCCGTGT CCCAGAACC CTCCCTCCGA     1894

TTTCTGTGGC GGGAGCTGAG TTGGCAGTTC TGCTATAAAC TGTCTGAAGT CACTAAACGT    1954

TTTACGGTGA ACGGGTTGTC CATCCAGCTT ACGGCTAAAA TGGTCAGTCG TGGAGAAATC    2014

CACGCCAGCA GATTTACAAA TCTCTGAGGC GCCTTTGAAA CCATCTCCTA GGTTTTTTCG    2074

GAAGGACTTC GGTCCGTGTA CCTCTAGCAC AACGTGCTAG TCTTAGGGTA CGGGTGCCCC    2134

TTGTCTTCGC ACCTTCGTGG GGGCTCCAAA AGGAGACCA                           2173
```

(2) INFORMATION FOR SEQ ID NO:7:

(i) SEQUENCE CHARACTERISTICS:
        (A) LENGTH: 264 amino acids
        (B) TYPE: amino acid
        (D) TOPOLOGY: linear (ii) MOLECULE TYPE: protein (xi) SEQUENCE DESCRIPTION: SEQ ID NO:7:

```
Met Ala Leu Val Val Lys Gly Lys Val Asn Ile Asn Glu Phe Ile Asp
 1               5                  10                  15

Leu Ser Lys Ser Glu Lys Leu Leu Pro Ser Met Phe Thr Pro Val Lys
                20                  25                  30

Ser Val Met Val Ser Lys Val Asp Lys Ile Met Val His Glu Asn Glu
            35                  40                  45

Ser Leu Ser Glu Val Asn Leu Leu Lys Gly Val Lys Leu Ile Glu Gly
        50                  55                  60

Gly Tyr Val Cys Leu Val Gly Leu Val Val Ser Gly Glu Trp Asn Phe
65                  70                  75                  80

Pro Asp Asn Arg Arg Gly Gly Val Ser Val Cys Met Val Asp Lys Arg
                85                  90                  95

Met Glu Arg Ala Asp Glu Ala Thr Leu Gly Ser Tyr Tyr Thr Ala Ala
                100                 105                 110

Ala Lys Lys Arg Phe Gln Phe Lys Val Val Pro Asn Tyr Gly Ile Thr
            115                 120                 125

Thr Lys Asp Ala Glu Lys Asn Ile Trp Gln Val Leu Val Asn Ile Lys
        130                 135                 140

Asn Val Lys Met Ser Ala Gly Tyr Cys Pro Leu Ser Leu Glu Phe Val
145                 150                 155                 160

Ser Val Cys Ile Val Tyr Lys Asn Asn Ile Lys Leu Gly Leu Arg Glu
                165                 170                 175

Lys Val Thr Ser Val Asn Asp Gly Gly Pro Met Glu Leu Ser Glu Glu
                180                 185                 190

Val Val Asp Glu Phe Met Glu Asn Val Pro Met Ser Val Arg Leu Ala
            195                 200                 205

Lys Phe Arg Thr Lys Ser Ser Lys Arg Gly Pro Lys Asn Asn Asn Asn
        210                 215                 220

Leu Gly Lys Gly Arg Ser Gly Gly Arg Pro Lys Pro Lys Ser Phe Asp
225                 230                 235                 240

Glu Val Glu Lys Glu Phe Asp Asn Leu Ile Glu Asp Glu Ala Glu Thr
```

```
                        245              250              255
Ser Val Ala Asp Ser Asp Ser Tyr
        260

(2) INFORMATION FOR SEQ ID NO:8:

(i) SEQUENCE CHARACTERISTICS:
        (A) LENGTH: 2621 base pairs
        (B) TYPE: nucleic acid
        (C) STRANDEDNESS: single
        (D) TOPOLOGY: unknown (vi) ORIGINAL SOURCE:
         (A) ORGANISM: Chimeric tomato spotted wilt virus S RNA (xi) SEQUENCE DESCRIPTION: SEQ ID NO:8:

AGAGCAATCG TGTCAATTTT GTGTTCATAC CTTAACACTC AGTCTTACAA ATCATCACAT      60

TAAGAACCTA AGAAACGACT GCGGGATACA GAGTTGCACT TTCGCACCTT GAGTTACATA     120

CGGTCAAAGC ATATAACAAC TTTTACGATC ACCATGGCTT ACTCAATCAC TTCTCCATCG     180

CAATTTGTGT TTTTGTCATC TGTATGGGCT GACCCTATAG AATTGTTAAA CGTTTGTACA     240

AATTCGTTAG GTAACCAGTT TCAAACACAG CAAGCAAGAA CTACTGTTCA ACAGCAGTTC     300

AGCGAGGTGT GGAAACCTTT CCCTCAGAGC ACCGTCAGAT TTCCTGGCGA TGTTTATAAG     360

GTGTACAGGT ACAATGCAGT TTTAGATCCT CTAATTACTG CGTTGCTGGG GTCTTTCGAT     420

ACTAGGAATA GAATAATCGA AGTAGAAAAC CAGCAGAATC CGACAACAGC TGAAACGTTA     480

GATGCTACCC GCAGGGTAGA CGACGCTACG GTTGCAATTC GGTCTGCTAT AAATAATTTA     540

GTTAATGAAC TAGTAAGAGG TACTGGACTG TACAATCAAA ATACTTTTGA AAGTATGTCT     600

GGGTTGGTCT GGACCTCTGC ACCTGCATCT TAAATCCATG GCTGTAAGTT AAATTATAAA     660

AAAGCCTATA AATATATAAA GCTTTCTTTA TCTTTATTGC TTGTGCTTGC TTAGTGTGTT     720

AAATTTTAAA TAAGTGTGTT TAATTAAAGT TTGCTTTCTG TGTGTTGTGC TTAATAAATA     780

ATAAAATAAC AAAAACAACG AAAACAAAAA ATAAATAAAA TAAAAATAAA ATAAAAATAA     840

AATAAAAATAA AAATAAAATA AAAAATAAAA AACAAAAAAC AAAAAACAAA AACAAAACCC     900

AAATTTGGCC AAATTGGTCC CTTTCGGGTC TTTTTGGTTT TTCGTTTTTT AATTTTTTGT     960

TGTTTTTATT TCATTTTTTG ATTTTATTTT ATTTTAATTT TATTTTCATT TTTATTTTTT    1020

GTTTTTATGG TTTCTACTAG ACAGGAGGAA TTTGAAAGAG ATGACAAACA GAGAAATAAT    1080

TATAAGTAAA GAAAGAAAAT AAACATAACA TAATTAGAAA AAGCTGGACA AAGCAAGATT    1140

ATTTTGATCC TGAAGCATAC GCTTCCTTAA CCTTAGATTC TTTCTTTTTG ATCCCGCTTA    1200

AATCAAGCTT TAACAAAGAT TTTGCAACTG AAATAGATTG TGGAGAAATT TTAATTTCTC    1260

CTCTGGCAAA GTCTATCTTC CATGAAGGGA TTTGGATGCT GTCTAAGTAA GACATAGTTT    1320

GTGTGTTAGA TGGAAGACAT TCAAGTGTTT TTGAAAGGAA ATATTTCCTT TTGTAGGCAT    1380

CTTCACTGTA ATTCAAGGTT CTTTCACCTA AATCTAACTT TCCAGGAGTT AGCTCAAGGT    1440

TGTTCAAAGT GTAGATGATT ACATCTTCTT GCAAGTTAGT TGCAAAGAAC TTGTGCAAAG    1500

ATGTGTGAGT TTCGAGCCAG AGCATTGGAA CCGATCCTTT GGGGTATGAA GGGTCATGAA    1560

CAATGTTGTA AGGCTCCTTT AAATCAGAAA ACATCATTGA TAATTCAAAA GGAGCTTTGC    1620

ATTTGCGAAT TGGGAGCTGA TGCTTGCAAA TAACAGTAAT GTTTAAAGCT GTCTCAACAC    1680

TGTTATGGTT TGGAATGCAG GCAATAGATA AATAAAATGT TTTGTTTGTT TCATCTCCTG    1740

CAACCTTGAA CAATTTCTGA ATGGAAACCT GCTTCAAAAC CTTTGGAACC CTTAGCCAGA    1800

GGCTCAGCTT GAAATGAGAA TCAGTGGAAG CTTGAGAGTT AGGCATGATG TTGTTTTCTG    1860
```

```
CTGACATGAG CAGAGATTTC ACTGCAAGAG AATTTACAGT TCTGTTGTTG CTTTCAACTT    1920

GATTGAAATT TGGCTTGAAA CTGTACAGCC ATTCATGGAC ATTTCTGTTA GGAGATAGAA    1980

CATTCACTTT GCCTAAAGCC TGATTATAGC ACATCTCGAT CTTATAGGTA TGCTCTTTGA    2040

CACAAGACAA AGAGCCTTTG TTTGCAGCTT CAATGTATTT GTCATTGGGA ATTATGTCTT    2100

TTTCTTGGAG CTGGAATCGG TCTGTAATAT CAGATCTGTT CATGATAGAT TCAATAGAGT    2160

GGAGCTGGGC AGGAGACAAA ACCTTCAAAT GACCTTGATG TTTCACTCCG TTAGCATTGA    2220

CTGTATTTGA GCAAACAGAT AGTGCCAGAA CAGAGTTATC AATATTGATG CTAAAATCAA    2280

TATCATCAAA AATAGGGATA TACACATGCT GAGAAAGAAA TCTCTTCTTC TTCACAGGGA    2340

AGATCCCTAC TTTGCAGTAT AGCCAAAGGA CTACTTTGCT TCTTGAATCA GAATACAGCT    2400

GGGTCTGAAC TAGTTGAGAA CCAGTACCAA GTTCATGAAT CCAGTAAGAA TCTACAACAG    2460

CTTTACCAGA TGCAGTTGAT CCCCAGACTG AAGCTCTTGT CTGAATGATC GACTCATAAA    2520

CACTTGAAGA CATTATGGTT ATTGGTACTG TGTTCTTATT ACAGTATTGT GATTTTCTAA    2580

GTGAGGTTTG ATTATGAACA AAATTCTGAC ACAATTGCTC T                        2621
```

(2) INFORMATION FOR SEQ ID NO:9:

(i) SEQUENCE CHARACTERISTICS:
        (A) LENGTH: 464 amino acids
        (B) TYPE: amino acid
        (C) STRANDEDNESS: single
        (D) TOPOLOGY: unknown (ii) MOLECULE TYPE: protein (vi) ORIGINAL SOURCE:
        (A) ORGANISM: Protein NSs (xi) SEQUENCE DESCRIPTION: SEQ ID NO:9:

```
Met Ser Ser Ser Val Tyr Glu Ser Ile Ile Gln Thr Arg Ala Ser Val
 1               5                  10                  15

Trp Gly Ser Thr Ala Ser Gly Lys Ala Val Val Asp Ser Tyr Trp Ile
            20                  25                  30

His Glu Leu Gly Thr Gly Ser Gln Leu Val Gln Thr Gln Leu Tyr Ser
        35                  40                  45

Asp Ser Arg Ser Lys Val Val Leu Trp Leu Tyr Cys Lys Val Gly Ile
    50                  55                  60

Phe Pro Val Lys Lys Arg Phe Leu Ser Gln His Val Tyr Ile Pro
65                  70                  75                  80

Ile Phe Asp Asp Ile Asp Phe Ser Ile Asn Ile Asp Asn Ser Val Leu
                85                  90                  95

Ala Leu Ser Val Cys Ser Asn Thr Val Asn Ala Asn Gly Val Lys His
            100                 105                 110

Gln Gly His Leu Lys Val Leu Ser Pro Ala Gln Leu His Ser Ile Glu
        115                 120                 125

Ser Ile Met Asn Arg Ser Asp Ile Thr Asp Arg Phe Gln Leu Gln Glu
    130                 135                 140

Lys Asp Ile Ile Pro Asn Asp Lys Tyr Ile Glu Ala Ala Asn Lys Gly
145                 150                 155                 160

Ser Leu Ser Cys Val Lys Glu His Thr Tyr Lys Ile Glu Met Cys Tyr
                165                 170                 175

Asn Gln Ala Leu Gly Lys Val Asn Val Leu Ser Pro Asn Arg Asn Val
            180                 185                 190

His Glu Trp Leu Tyr Ser Phe Lys Pro Asn Phe Asn Gln Val Glu Ser
```

```
                195                 200                 205
Asn Asn Arg Thr Val Asn Ser Leu Ala Val Lys Ser Leu Leu Met Ser
    210                 215                 220

Ala Glu Asn Asn Ile Met Pro Asn Ser Gln Ala Ser Thr Asp Ser His
225                 230                 235                 240

Phe Lys Leu Ser Leu Trp Leu Arg Val Pro Lys Val Leu Lys Gln Val
                245                 250                 255

Ser Ile Gln Lys Leu Phe Lys Val Ala Gly Asp Glu Thr Asn Lys Thr
            260                 265                 270

Phe Tyr Leu Ser Ile Ala Cys Ile Pro Asn His Asn Ser Val Glu Thr
        275                 280                 285

Ala Leu Asn Ile Thr Val Ile Cys Lys His Gln Leu Pro Ile Arg Lys
    290                 295                 300

Cys Lys Ala Pro Phe Glu Leu Ser Met Met Phe Ser Asp Leu Lys Glu
305                 310                 315                 320

Pro Tyr Asn Ile Val His Asp Pro Ser Tyr Pro Lys Gly Ser Val Pro
                325                 330                 335

Met Leu Trp Leu Glu Thr His Ser Leu His Lys Phe Phe Ala Thr
            340                 345                 350

Asn Leu Gln Glu Asp Val Ile Ile Tyr Thr Leu Asn Asn Leu Glu Leu
        355                 360                 365

Thr Pro Gly Lys Leu Asp Leu Gly Glu Arg Thr Leu Asn Tyr Ser Glu
    370                 375                 380

Asp Ala Tyr Lys Arg Lys Tyr Phe Leu Ser Lys Thr Leu Glu Cys Leu
385                 390                 395                 400

Pro Ser Asn Thr Gln Thr Met Ser Tyr Leu Asp Ser Ile Gln Ile Pro
                405                 410                 415

Ser Trp Lys Ile Asp Phe Ala Arg Gly Glu Ile Lys Ile Ser Pro Gln
            420                 425                 430

Ser Ile Ser Val Ala Lys Ser Leu Leu Lys Leu Asp Leu Ser Gly Ile
        435                 440                 445

Lys Lys Lys Glu Ser Lys Val Lys Glu Ala Tyr Ala Ser Gly Ser Lys
    450                 455                 460

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: unknown (iii) HYPOTHETICAL: NO (vi) ORIGINAL SOURCE:
         (A) ORGANISM: oligonucleotide (xi) SEQUENCE DESCRIPTION: SEQ ID NO:10:

TTTGGATCCA CGTGGTCTCC TTTTGGAG                                      28

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (iii) HYPOTHETICAL: NO (vi) ORIGINAL SOURCE:
```

(A) ORGANISM: oligonucleotide (xi) SEQUENCE DESCRIPTION: SEQ ID NO:11:

TTTGGATCCG TAATCTTACC ACT                                              23

(2) INFORMATION FOR SEQ ID NO:12:

(i) SEQUENCE CHARACTERISTICS:
        (A) LENGTH: 45 base pairs
        (B) TYPE: nucleic acid
        (C) STRANDEDNESS: single
        (D) TOPOLOGY: unknown (iii) HYPOTHETICAL: NO (vi) ORIGINAL SOURCE:
        (A) ORGANISM: oligonucleotide (xi) SEQUENCE DESCRIPTION: SEQ ID NO:12:

TTTGGATCCA GAGCAATCGT GTCAATTTTG TGTTCATACC TTAAC                       45

(2) INFORMATION FOR SEQ ID NO:13:

(i) SEQUENCE CHARACTERISTICS:
        (A) LENGTH: 52 base pairs
        (B) TYPE: nucleic acid
        (C) STRANDEDNESS: single
        (D) TOPOLOGY: unknown (iii) HYPOTHETICAL: NO (vi) ORIGINAL SOURCE:
        (A) ORGANISM: oligonucleotide (xi) SEQUENCE DESCRIPTION: SEQ ID NO:13:

TTTGGATCCA GAGCAATTGT GTCAGAATTT TGTTCATAAT CAAACCTCAC TT              52

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (iii) HYPOTHETICAL: NO (vi) ORIGINAL SOURCE:
        (A) ORGANISM: oligonucleotide (xi) SEQUENCE DESCRIPTION: SEQ ID NO:14:

GTATTAACCA TGGCTTACTC                                                  20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (iii) HYPOTHETICAL: NO (vi) ORIGINAL SOURCE:
        (A) ORGANISM: oligonucleotide (xi) SEQUENCE DESCRIPTION: SEQ ID NO:15:

GCACCCATGG ATTTAAGATG                                                  20

(2) INFORMATION FOR SEQ ID NO:16:

(i) SEQUENCE CHARACTERISTICS:
            (A) LENGTH: 20 base pairs
            (B) TYPE: nucleic acid
            (C) STRANDEDNESS: single
            (D) TOPOLOGY: unknown (iii) HYPOTHETICAL: NO (vi) ORIGINAL SOURCE:
            (A) ORGANISM: oligonucleotide (xi) SEQUENCE DESCRIPTION: SEQ ID NO:16:

TATTTCTCCA TGGCTCTAGT                                                      20

(2) INFORMATION FOR SEQ ID NO:17:

(i) SEQUENCE CHARACTERISTICS:
            (A) LENGTH: 20 base pairs
            (B) TYPE: nucleic acid
            (C) STRANDEDNESS: single
            (D) TOPOLOGY: unknown (iii) HYPOTHETICAL: NO (vi) ORIGINAL SOURCE:
            (A) ORGANISM: oligonucleotide (xi) SEQUENCE DESCRIPTION: SEQ ID NO:17:

GAGTAAGCCA TGGTTAATAC                                                      20

(2) INFORMATION FOR SEQ ID NO:18:

(i) SEQUENCE CHARACTERISTICS:
            (A) LENGTH: 176 base pairs
            (B) TYPE: nucleic acid
            (C) STRANDEDNESS: single
            (D) TOPOLOGY: unknown (iii) HYPOTHETICAL: NO (vi) ORIGINAL SOURCE:
            (A) ORGANISM: oligonucleotide (xi) SEQUENCE DESCRIPTION: SEQ ID NO:18:

TTTCCATGGC ATGCGACTAC ACTTGCGGTT CTAACTGCTA CTCTTCTTCA GACGTTTCTA          60

CTGCTCAAGC TGCCGGATAT AAACTTCACG AAGACGGTGA AACTGTTGGA TCTAATTCTT         120

ACCCACACAA ATACAACAAC TACGAAGGTT TTGATTTCTC TGTGAGCTCT CCCTAC            176

(2) INFORMATION FOR SEQ ID NO:19:

(i) SEQUENCE CHARACTERISTICS:
            (A) LENGTH: 170 base pairs
            (B) TYPE: nucleic acid
            (C) STRANDEDNESS: single
            (D) TOPOLOGY: unknown (iii) HYPOTHETICAL: NO (vi) ORIGINAL SOURCE:
            (A) ORGANISM: oligonucleotide (xi) SEQUENCE DESCRIPTION: SEQ ID NO:19:

GGGCCATGGT TATGTACATT CAACGAAGTT GTTACCAGAA GCACCAGTGT GAGTGATAAC          60

ACCAGCATGT TGGTTGTTTT CGTTGAAGAC GACACGGTCA GCACCTGGAG AAGGACCAGA        120

GTAAACATCA CCGCTAGAGA GGATAGGCCA TTCGTAGTAG GGAGAGCTCA                   170

(2) INFORMATION FOR SEQ ID NO:20:

(i) SEQUENCE CHARACTERISTICS:
            (A) LENGTH: 18 base pairs
            (B) TYPE: nucleic acid
            (C) STRANDEDNESS: single
            (D) TOPOLOGY: unknown (iii) HYPOTHETICAL: NO (vi) ORIGINAL SOURCE:
            (A) ORGANISM: oligonucleotide (xi) SEQUENCE DESCRIPTION: SEQ ID NO:20:

CCACGTCTTC AAAGCAAG                                                     18

(2) INFORMATION FOR SEQ ID NO:21:

(i) SEQUENCE CHARACTERISTICS:
            (A) LENGTH: 50 base pairs
            (B) TYPE: nucleic acid
            (C) STRANDEDNESS: single
            (D) TOPOLOGY: unknown (iii) HYPOTHETICAL: NO (vi) ORIGINAL SOURCE:
            (A) ORGANISM: oligonucleotide (xi) SEQUENCE DESCRIPTION: SEQ ID NO:21:

CTTCGCACCT TCGTGGGGGC TCCAAAAGGA GACCACCTCT CCAAATGAAA                  50

(2) INFORMATION FOR SEQ ID NO:22:

(i) SEQUENCE CHARACTERISTICS:
            (A) LENGTH: 21 base pairs
            (B) TYPE: nucleic acid
            (C) STRANDEDNESS: single
            (D) TOPOLOGY: unknown (iii) HYPOTHETICAL: NO (vi) ORIGINAL SOURCE:
            (A) ORGANISM: oligonucleotide (xi) SEQUENCE DESCRIPTION: SEQ ID NO:22:

AGCTGCTAAC GTCTTATTAA G                                                 21

(2) INFORMATION FOR SEQ ID NO:23:

(i) SEQUENCE CHARACTERISTICS:
            (A) LENGTH: 18 base pairs
            (B) TYPE: nucleic acid
            (C) STRANDEDNESS: single
            (D) TOPOLOGY: unknown (iii) HYPOTHETICAL: NO (vi) ORIGINAL SOURCE:
            (A) ORGANISM: oligonucleotide (xi) SEQUENCE DESCRIPTION: SEQ ID NO:23:

GTCTTTAGCA CCATGGTG                                                     18

(2) INFORMATION FOR SEQ ID NO:24:

(i) SEQUENCE CHARACTERISTICS:
            (A) LENGTH: 18 base pairs
            (B) TYPE: nucleic acid
            (C) STRANDEDNESS: single
            (D) TOPOLOGY: unknown (iii) HYPOTHETICAL: NO (vi) ORIGINAL SOURCE:
     (A) ORGANISM: oligonucleotide (xi) SEQUENCE DESCRIPTION: SEQ ID NO:24:

GGAGAGCCAT GGCTCGGG                                                          18

(2) INFORMATION FOR SEQ ID NO:25:

(i) SEQUENCE CHARACTERISTICS:
        (A) LENGTH: 105 base pairs
        (B) TYPE: nucleic acid
        (C) STRANDEDNESS: single
        (D) TOPOLOGY: unknown (iii) HYPOTHETICAL: NO (vi) ORIGINAL SOURCE:
         (A) ORGANISM: oligonucleotide (xi) SEQUENCE DESCRIPTION: SEQ ID NO:25:

TTTCTGCAGA TCTTAGCCAT CCGAGTGGAC GTGCGTCCTC CTTCGGATGC CCAGGTCGGA            60

CCGCGAGGAG GTGGAGATGC CATGCCGACC CGTAATCTTA CCACT                           105

(2) INFORMATION FOR SEQ ID NO:26:

(i) SEQUENCE CHARACTERISTICS:
        (A) LENGTH: 28 base pairs
        (B) TYPE: nucleic acid
        (C) STRANDEDNESS: single
        (D) TOPOLOGY: unknown (iii) HYPOTHETICAL: NO (vi) ORIGINAL SOURCE:
         (A) ORGANISM: oligonucleotide (xi) SEQUENCE DESCRIPTION: SEQ ID NO:26:

ACACAATTGC TCTCCTCTCC AAATGAAA                                               28

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (iii) HYPOTHETICAL: NO (vi) ORIGINAL SOURCE:
         (A) ORGANISM: oligonucleotide (xi) SEQUENCE DESCRIPTION: SEQ ID NO:27:

GACCCGAAAG GGACCAATTT                                                        20

(2) INFORMATION FOR SEQ ID NO:28:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (iii) HYPOTHETICAL: NO (vi) ORIGINAL SOURCE:
         (A) ORGANISM: oligonucleotide (xi) SEQUENCE DESCRIPTION: SEQ ID NO:28:

```
TTTCCATGGC TGTAAGTTAA ATT                                                    23

(2) INFORMATION FOR SEQ ID NO:29:

(i) SEQUENCE CHARACTERISTICS:
         (A) LENGTH: 21 base pairs
         (B) TYPE: nucleic acid
         (C) STRANDEDNESS: single
         (D) TOPOLOGY: unknown (iii) HYPOTHETICAL: NO (vi) ORIGINAL SOURCE:
         (A) ORGANISM: oligonucleotide (xi) SEQUENCE DESCRIPTION: SEQ ID NO:29:

TTTCCATGGT GATCGTAAAA G                                                      21

(2) INFORMATION FOR SEQ ID NO:30:

(i) SEQUENCE CHARACTERISTICS:
         (A) LENGTH: 105 base pairs
         (B) TYPE: nucleic acid
         (C) STRANDEDNESS: single
         (D) TOPOLOGY: unknown (iii) HYPOTHETICAL: NO (vi) ORIGINAL SOURCE:
         (A) ORGANISM: oligonucleotide (xi) SEQUENCE DESCRIPTION: SEQ ID NO:30:

TTTCTGCAGA TCTTAGCCAT CCGAGTGGAC GTGCGTCCTC CTTCGGATGC CCAGGTCGGA            60

CCGCGAGGAG GTGGAGATGC CATGCCGACC CAGAGCAATC GTGTC                           105
```

PLANT VIRUS DNA CONSTRUCTS AND VIRUS RESISTANT PLANTS COMPRISING SAID CONSTRUCTS

BACKGROUND

The present invention relates to pathogen resistant plants and in particular to pathogen resistant plants wherein pathogen resistance is triggered in response to invading pathogens such as viruses, DNA constructs for use in such plants and methods of introducing virus induced resistance into plants.

Viral infections in plants are frequently responsible for detrimental effects in growth, undesirable morphological changes, decreased yield and the like. Such infections often result in a higher susceptibility to infection in infected plants to other plant pathogens and plant pests.

Virus particles generally comprise a relatively small amount of genetic material (single or double stranded RNA or DNA) protected by a protein or proteins which in some viral types can also be surrounded with host-derived lipid membranes, yielding infectious particles. Viruses are dependent on host cells for multiplication and may therefore be regarded as intracellular parasites.

Plants have evolved a number of defensive mechanisms to limit the effects of viral infection. For example, so-called horizontal or partial resistances which are polygenic in nature and so-called vertical resistances which are monogenic in nature.

Horizontal resistance is difficult to introduce successfully into plants in breeding programs, however, vertical resistance can be bred into plants relatively easily within plant breeding programs. Genes coding for virus resistance can act constitutively in a passive sense, ie without a requirement for inducing gene expression. Constitutively expressed virus resistances include as modes of action non-host resistances, tolerance ie inhibition of disease establishment, immunity ie inhibition of transport or the presence of antiviral agents and the like. Alternatively, genes coding for virus resistance in plants can be actively switched on by way of inducing expression of a gene or genes encoding for a viral resistance. An example of such a system includes the hypersensitive response.

So-called hypersensitive responses (HSR) in plants have been reported and are generally characterized by death of plant cells in the vicinity of the penetrating pathogen shortly after infection. Movement of the pathogen through infected or invaded cells is restricted or blocked due to necrosis of the invaded cell and/or cells in the environs of the invaded cell(s). In addition, HSR involves a cascade of additional or secondary defense responses and the accumulation of certain proteins and secondary metabolites, leading to a general increased level of resistance to attack by pathogens. HSR reactions to invading organisms are generally thought to involve a resistance gene product in the plant cell which recognizes and interacts with an elicitor element, ie the product of an avirulence gene of a pathogen. Elicitor element recognition in the cells of a resistant plant triggers an HSR reaction which in its turn restricts the pathogen infection to a single cell or cells, or at most to a few plant cells in the immediate vicinity thereof.

An example of HSR-mediated resistance to virus infection is that of tobacco plants harbouring the N' resistance gene to tobamoviruses such as TMV and ToMV, which contain the coat protein avirulence gene. Thus far, more than twenty single dominant HSR-type resistance genes have been identified, and are present in many agronomically important crops including tobacco, tomato, potato, pepper, lettuce, and the like.

Despite the apparent abundance of resistance sources to certain viruses, many crops still lack effective resistance genes to important viral pathogens [Fraser, R. S. S. (1992). Euphytica 63:175]. Searching of wild type germplasm collections has identified only a few suitable sources of viral resistance capable of being introduced successfully into agronomically important crops. An example is the absence of vertical resistance genes to cucumber mosaic virus (CMV) in many agronomically important crop types including but not limited to tomato, pepper, cucumber, melon, lettuce and the like.

Plant breeders continuously try to develop varieties of crop plant species tolerant to or resistant to specific virus strains. In the past, virus resistance conferring genes have been transferred from wild types related to commercial plants into commercial varieties through breeding. The transfer of an existing resistance in the wild from the wild type gene pool to a cultivar is a tedious process in which the resistance conferring gene(s) must first be identified in a source (donor) plant species and then combined into the gene pool of a commercial variety. Resistance or tolerance generated in this way is typically active only against one or at best a few strains of the virus in question. A further disadvantage is that the breeding programme generally takes a long time, measured in years, in getting to agronomically useful plants.

In an alternative, a system referred to as "cross-protection" has been employed. Cross-protection is a phenomenon in which infection of a plant with one strain of a virus protects that plant against superinfection with a second related virus strain. The cross-protection method preferentially involves the use of avirulent virus strains to infect plants, which act to inhibit a secondary infection with a virulent strain of the same virus. However, the use of a natural cross-protection system can have several disadvantages. The method is very labour intensive because it requires inoculation of each individual plant crop, and carries the risk that an avirulent strain may mutate to a virulent strain, thus becoming a causal agent for crop disease in itself. A further possible hazard is that an avirulent virus strain in one plant species can act as a virulent strain in another plant species.

Genetically engineered cross-protection is a form of virus resistance which phenotypically resembles natural cross-protection, but is achieved through the expression of genetic information of a viral coat protein from the genome of a genetically manipulated plant. It is known that expression of the tobacco mosaic virus strain U1 (TMV-U1) coat protein gene from the genome of a transgenic plant can result in a delay of symptom development after infection with any TMV strain. Similarly, coat protein-mediated protection has also been obtained for alfalfa mosaic virus (AMV), potato virus X (PVX) and cucumber mosaic virus (CMV). For some plant viruses, eg luteoviruses, it is difficult to obtain detectable amounts of the corresponding coat protein in a transgenic plant, and consequently, virus resistance is generally lowered. Furthermore, any alleged degree of protection requires that the plant produces coat protein continually and thus imposes an energy burden on the plant. As a result of such limitations the commercial value of such technology remains unclear.

A further example of genetically engineered virus resistance includes the introduction of plant viral satellite RNA wherein expression of incorporated genetic material modifies the plant virus or its effects.

An object of the present invention is to provide an alternative more reliable engineered virus resistance strategy in plants to those engineered resistances known in the art, based on direct pathogen induced expression of molecules in target tissues of a plant before the invading pathogen can establish itself in the host plant.

Another object of the invention is to combine genetic engineering plant transformation technology with naturally existing plant viral defense mechanisms in plant tissue.

DETAILED DESCRIPTION

According to the present invention there is provided a plant virus DNA construct capable of encoding directly or indirectly for a minus sense RNA molecule capable of interacting with an RNA dependent RNA polymerase encoded for by an invading virus such that at least one eliciting element is produced as a consequence of the interaction with the RNA dependent RNA polymerase encoded by the said invading virus.

In another embodiment of the invention there is provided a plant virus recombinant DNA construct capable of encoding for a plus sense RNA molecule capable of interacting with an RNA dependent RNA polymerase encoded for by an invading virus producing as a result of such interaction, a plus sense RNA molecule which is capable of encoding for at least one eliciting element capable of eliciting a natural plant defense in the plant on invasion of the plant by the said invading virus.

The plant virus DNA construct can be derived from any virus source capable of attacking a plant, however it is preferred that the plant virus DNA is derived from any virus source which is known to attack, is suspected of attacking or is capable of attacking an agronomically attractive plant type. It can be a natural plant virus DNA suitably modified for expression or it may be derived synthetically. The plant virus DNA should be capable of encoding for transcription into an RNA sequence complementary (ie minus sense) to a viral RNA (ie plus sense) in plant cells. In addition, the plant virus DNA should contain a portion or segment thereof which when transcribed to yield minus sense RNA and further transcribed to plus sense RNA, upon translation of the plus sense RNA, is capable of giving rise to at least one eliciting element or part thereof sufficient to elicit a natural plant defense mechanism against an invading virus. Suitable plant virus DNA or RNA sources are those derived from plant viruses capable of invading plant types such as tomatoes, peppers, melons, lettuces, cauliflowers, broccolis, cabbages, brussels sprouts, sugar beet, corn (maize), sweetcorn, onions, carrots, leeks, cucumbers, tobacco and the like. Also included as plant virus DNA or RNA sources are those derived from plant viruses capable of invading plant types from ornamental crops such as Impatiens, begonia, petunia, pelargoniums (geraniums, viola, cyclamen, verbena, vinca, tagetes, primula, saintpaulia and the like.

A minus sense RNA molecule is one which contains at least a cistron or part thereof corresponding to at least a portion of the said plant virus DNA and is capable of giving rise to a plus sense RNA molecule transcribable from the said minus sense RNA molecule which is capable of coding for and giving rise to at least one eliciting element or part thereof in plant cells. The minus sense RNA may be directly transcribable from the said plant virus DNA or it may be transcribable from a plus sense RNA derived from the said DNA. As such, the minus sense RNA transcribable from a plus sense RNA is referred to, for the purposes of the present invention, as being indirectly transcribable from the said DNA. The orientation or polarity of the cistron or cistrons or parts thereof located on the minus sense RNA molecule can be such that the eliciting element may not be directly coded for after transcription from the plant virus DNA construct. The genetic code of the cistron or cistrons or parts thereof is located on the complementary strand to the minus sense RNA molecule ie the plus sense RNA. The cistron coding for an eliciting element becomes available for translation when the minus sense viral RNA sequence is replicated by an RNA dependent RNA polymerase encoded for by an invading virus to yield a plus sense RNA molecule.

Minus sense RNA herein also includes those RNA molecules which can be described as having ambisense characteristics, such as RNA molecules from tospoviruses and the like. In such cases, the minus sense RNA contains at least a cistron corresponding to a portion of the said plant virus DNA and is capable of giving rise to a plus sense RNA transcribable from the said minus sense RNA which is capable of coding for and giving rise to at least one eliciting element or part thereof in plant cells.

A plus sense viral RNA molecule is one which is capable of directly or indirectly encoding at least one eliciting element or part thereof capable of being expressed in, and having a natural or engineered plant defense eliciting activity in plant cells. A plus sense RNA molecule is also one which is complementary to a viral minus sense RNA and is capable of giving rise directly or indirectly to at least one elicitor element upon translation in plant cells. Thus, a viral sense RNA molecule can be viewed as a complementary RNA molecule to a minus sense RNA molecule.

Plus sense RNA herein also includes those RNA molecules which can be described as having ambisense characteristics. In such cases, the plus sense RNA contains at least a cistron corresponding to a portion of the said plant virus DNA and is capable of directly coding for and giving rise to at least one eliciting element or part thereof in plant cells.

The amount of eliciting element which is expressed in the plant cell must be sufficient to elicit at least a cellular plant defense response against an invading virus resulting in a natural or engineered plant reaction effective in blocking or restricting further viral action. Thus, plus sense RNA molecules whether they be the complement of a minus sense RNA or an ambisense RNA must be capable of giving rise to elicitor elements which are capable of triggering or eliciting a natural or engineered plant defence response, whether that be through direct translation or through interaction with a viral RNA dependent RNA polymerase (eg via a generated subgenomic RNA). There can be one or more eliciting elements ultimately encoded by the plus sense RNA depending on the type of plant defense response/plant defence responses being elicited. The viral plus sense RNA sequence is preferably one wherein at least a viral cistron has been replaced by at least a cistron coding for an eliciting element capable of being expressed in plant cells, and having a natural or engineered plant defense eliciting activity in plant tissue.

The eliciting element can be any element translatable from a plus sense RNA cistron derivable from a plant virus DNA as hereinbefore described, and can be a protein, polypeptide, or peptide or fragments thereof. Examples of preferred eliciting elements include the so-called elicitor proteins and/or cell inhibitory proteins.

An elicitor protein is one which if present in plant tissue, is capable of eliciting, triggering, or inducing a hypersensitive response (HSR), that is a natural plant defense mechanism against invading pathogens such as viruses. Elicitor proteins can be of plant virus origin, such as coat proteins, proteins involved in cell-to-cell movement, helicases, RNA-dependent RNA polymerases and the like. In addition, elicitor proteins can originate from or be derived from other plant pathogens such as bacteria, fungi, nematodes and the like.

A cell inhibitory protein is a protein which if present in plant tissue, has a detrimental effect on the plant cell, leading to inhibition of cell growth eg cell division, and/or cell death. Cell inhibitory agents include but are not restricted to ribonucleases, proteinases, ribosomal inhibitory proteins, cell wall degrading proteins and the like.

The minus and plus sense RNA molecules can be viewed as plant virus RNAs since they are derived from a plant DNA construct as hereinbefore described and comprise the genome or a segment of the genome of a plant virus. In such plant virus RNAs, selected nucleotide fragments can be replaced by others or can be deleted. Replacement and/or deletion of nucleotides or segments comprised of nucleotides should be such so as not to interfere with the capability of the RNA molecule to multiply or replicate in virus-infected plant cells. Also, replacement and/or deletion of nucleotides, codons or segments comprised of nucleotides should be such so as not to interfere with the ability of the RNA dependent RNA polymerase of the invading virus to recognise and act upon an RNA molecule (in plus or minus sense orientation), and thereby initiating the sequence of events as described herein leading to the production of an effective amount of an eliciting element capable of eliciting a natural or engineered plant defense response. Examples of suitable plant virus RNA molecules include, but are not limited to genomic RNA molecules or segments thereof selected from the group comprising potyviruses, potexviruses, tobamoviruses, luteoviruses or genomic RNA or segments thereof of cucumoviruses, bromoviruses, tospoviruses and the like.

The plant virus DNA is under expression control of a promoter capable of functioning in plants and includes a terminator capable of functioning in plants.

A promoter is the nucleotide sequence upstream from the transcriptional initiation site and which contains all the regulatory regions required for transcription. Examples of promoters suitable for use in DNA constructs of the present invention include viral, fungal, bacterial, animal and plant-derived promoters capable of functioning in plant cells. A preferred promoter should express the DNA constitutively, that is in all living tissues of the plant. It will be appreciated that the promoter employed should give rise to the expression of the viral plant DNA at a rate sufficient to produce the amount of RNA capable of encoding for at least an elicitor element capable of eliciting a natural plant defense in a transformed plant on invasion of the plant by a virus. The required amount of RNA to be transcribed may vary with the type of plant. Examples of suitable promoters include the cauliflower mosaic virus 35S (CaMV 35S) and 19S (CaMV 19S) promoters, the nopaline synthase and octopine synthase promoters, the heat shock 80 (hsp80) promoter and the like.

A terminator is contemplated as (A) a DNA sequence downstream of the viral DNA, coding for transcription into an RNA sequence which is capable of autocatalytical, self cleavage, to release the terminator sequences from the recombinant viral RNA sequence, followed by (B) a DNA sequence at the end of a transcriptional unit which signals termination of transcription. These elements are 3'-non-translated sequences containing polyadenylation signals, which act to cause the addition of poly adenylate sequences to the 3' end of primary transcripts. Examples of sequences mentioned under (A) include self-cleaving RNA molecules or ribozymes such as ribonuclease P, Tetrahymena L-19 intervening sequence, hammerhead ribozymes, Hepatitis delta virus RNA, Neurospora mitochondrial VS RNA and the like [Symons, R. H. (1992). Ann. Rev. Biochem. 61:641]. Sequences mentioned under (B) may be isolated from funghi, bacteria, animals and/or plants. Examples, particularly suitable for use in the DNA constructs of the invention include the nopaline synthase polyadenylation signal of *Agrobacterium tumefaciens*, the 35S polyadenylation signal of CaMV and the zein polyadenylation signal from *Zea mays*.

A DNA or RNA sequence is complementary to another DNA or RNA sequence if it is able to form a hydrogen-bonded complex with it, according to rules of base pairing under appropriate hybridization conditions. For the purposes of the present invention appropriate hybridization conditions may include but are not limited to, for example, an incubation for about 16 hours at 42° C., in a buffer system comprising 5×standard saline citrate (SSC), 0.5% sodium dodecylsulphate (SDS), 5×Denhardt's solution, 50% formamide and 100 $\mu$g/ml carrier DNA or RNA (hereinafter the buffer system), followed by washing 3× in buffer comprising 1×SSC and 0.1% SDS at 65° C. for approximately an hour each time. Thus the hybridisation signal obtained for an RNA or DNA molecule, for example an autoradiogram reading, should be sufficiently clear to the man skilled in the art so as to suggest that an RNA or DNA molecule obtained could usefully be employed in the construction of plant virus DNA constructs suitable for use in the invention. Naturally, such an RNA or DNA molecule should be capable of the requisite activity as described herein. Thus replacement and/or deletion of nucleotides, codons or segments comprised of nucleotides should be such so as not to interfere with the ability of a DNA construct of the invention to code for a minus sense RNA molecule as herein described which is capable of being recognised by and of interaction with an RNA dependent RNA polymerase of an invading virus and thereby initiating the sequence of events as described herein leading to the production of an effective amount of an eliciting element capable of eliciting a natural or engineered plant defense response.

Suitable hybridization conditions employed in the present invention can involve incubation in a buffer system for about 16 hours at 49° C. and washing 3× in a buffer comprising 0.1×SSC and 0.1% SDS at 55° C. for about an hour each time. More preferably, hybridization conditions can involve incubation in a buffer system for about 16 hours at 55° C. and washing 3× in a buffer comprising 0.1×SSC and 0.1% SDS at 65° C. for approximately an hour each time. Naturally, any RNA or DNA molecule subjected to such hybridisation conditions should be capable of the requisite activity as described herein.

The invention also provides a vector capable of introducing the DNA construct of the invention into plants and methods of producing such vectors. The term vector employed herein refers to a vehicle by means of which DNA molecules or fragments thereof can be incorporated into a host organism. Suitable vehicles include plasmids, naked DNA introduced using micro-injection, particle guns, and the like [Offringa (1992). PhD thesis, State University Leiden, The Netherlands, Ch1:pages 7–28].

The term plants as used herein is used in a wide sense and refers to differentiated plants as well as undifferentiated plant material such as protoplasts, plant cells, seeds, plantlets and the like which under appropriate conditions can develop into mature plants, the progeny thereof and parts thereof such as cuttings and fruits of such plants.

The invention further provides plants comprising in their genome a DNA construct of the invention, and methods of producing such plants.

The plants according to the invention have reduced susceptibility to diseases caused by the respective viruses and do not have the disadvantages and limitations of plants obtained by classical methods and genetic engineering methods as discussed herein.

The invention is illustrated by the following non-limiting examples and accompanying figures.

Figure 1:
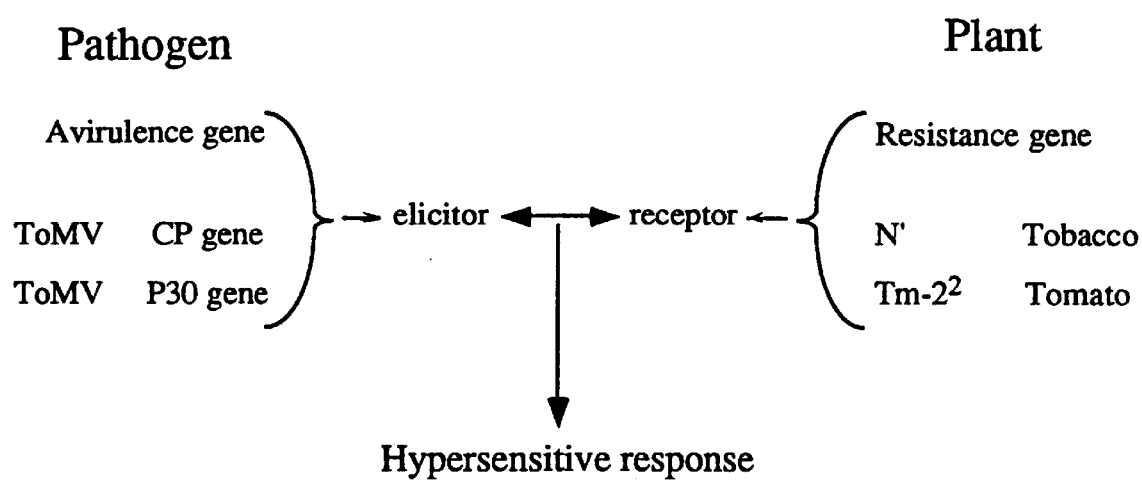
FIG. 1: Schematic representation of the interaction of pathogen and plant encoded proteins leading to induction of an HSR response.
Figure 2:
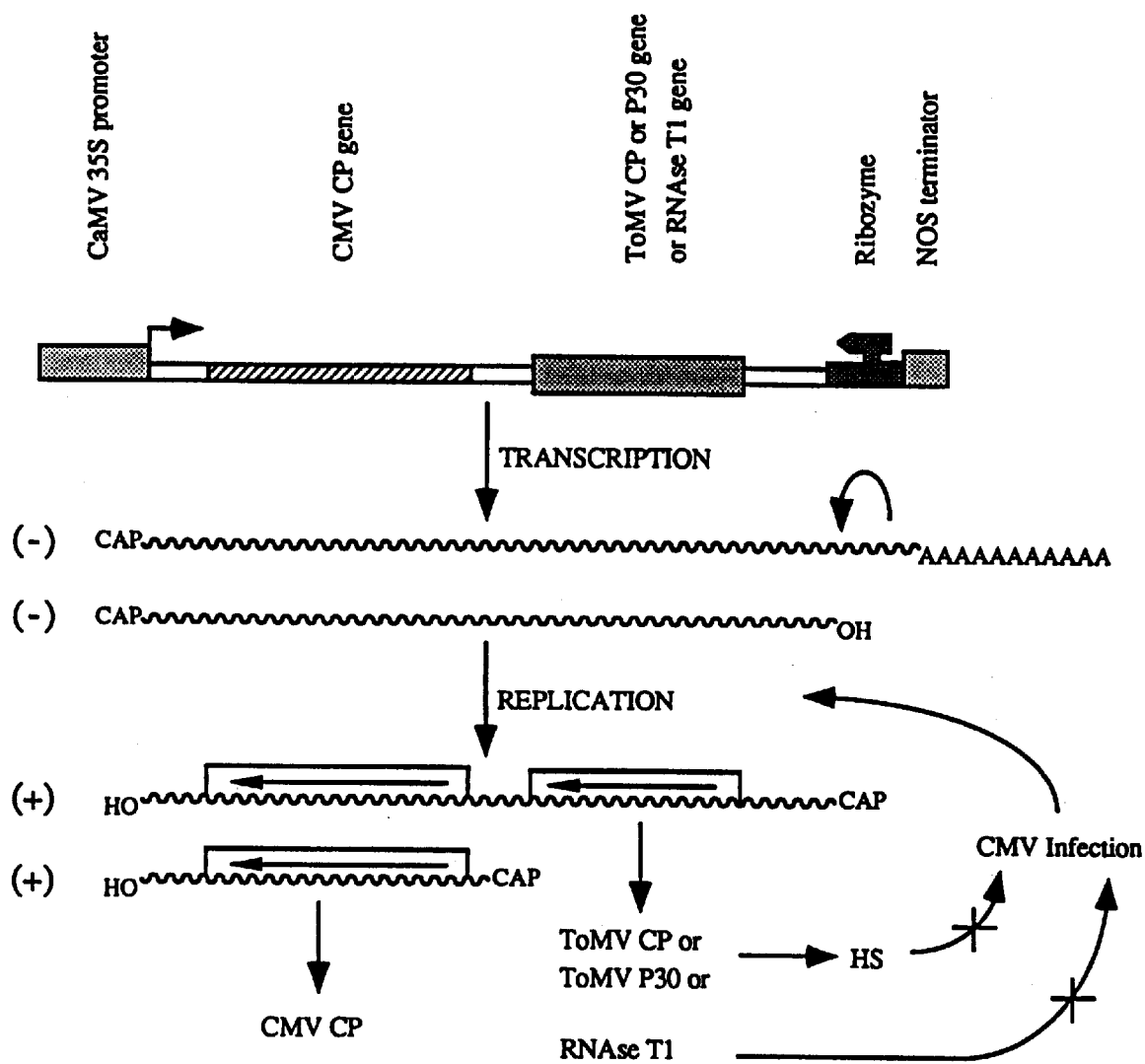
FIG. 2: Schematic representation of CMV resistant tobacco or tomato plants, obtained by expression of a minus-sense CMV RNA 3 molecule in which the MP gene is replaced by a gene coding for an elicitor (ToMV CP or P30) or a cell inhibitory protein (RNase T1).
Figure 3:
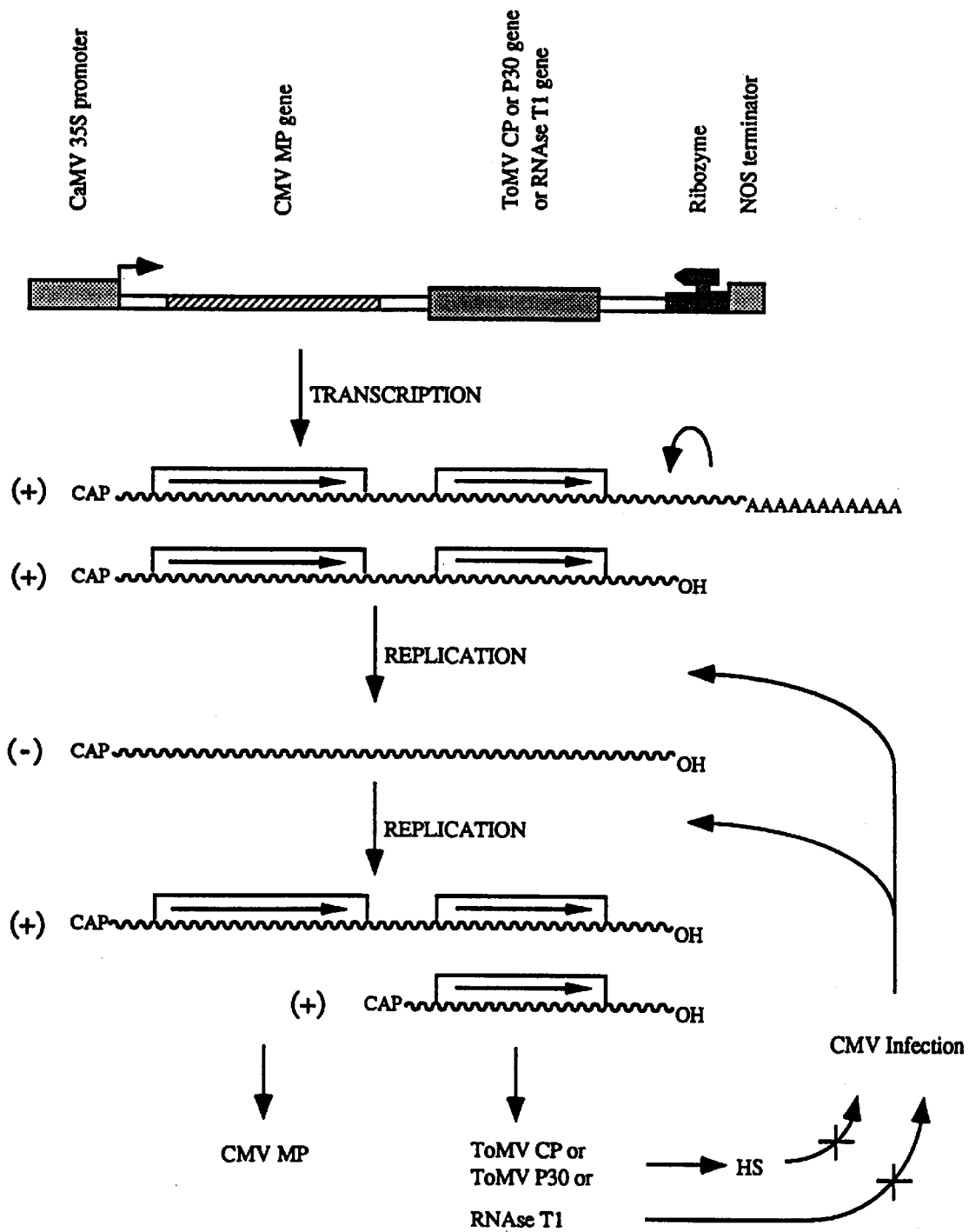
FIG. 3: Schematic representation of CMV resistant tobacco or tomato plants obtained by expression of a plus-sense CMV RNA 3 molecule in which the CP gene is replaced by a gene coding for an elicitor (ToMV CP or P30) or a cell inhibitory protein (RNase T1).

Sequence ID 1: Chimaeric cucumber mosaic virus RNA 3.

Sequence ID 2: Coat protein of ToMV (corresponding to nucleotides from positions 123–600 of Seq. ID. No.1).

Sequence ID 3: Coat protein of cucumber mosaic virus corresponding to nucleotide positions from 897–1550 of Seq. ID. No 1.

Sequence ID 4: Chimaeric cucumber mosaic virus RNA 3.

Sequence ID 5: RNAse T1 corresponding to positions 123–437 of Seq. ID No. 4.

Sequence ID 6: Chimaeric cucumber mosaic virus RNA 3, coding for P30 of ToMV.

Sequence ID 7: P30 of ToMV corresponding to nucleotide positions 123–914 of Seq. ID No.7.

Sequence ID 8: Chimaeric tomato spotted wilt virus S RNA, coding for the coat protein of ToMV and the non-structural protein, NSs in opposite polarity.

Sequence ID 9: The non-structural protein, NSs (in opposite polarity) corresponding to nucleotide positions 1141–2543 of Seq ID No.8.

EXAMPLES

All CMV, TSWV, and ToMV RNA-derived sequences presented here are depicted as DNA sequences for the sole purpose of uniformity. It will be appreciated that this is done for convenience only.

Cultivars of *Nicotiana tabacum* and *Lycopersicon esculentum*, used in plant transformation studies, are grown under standard greenhouse conditions. Axenic explant material is grown on standard MS media [Murashige and Skoog (1962). Physiol. Plant 15:473] containing appropriate phytohormones and sucrose concentrations.

*E. coli* bacteria are grown on rotary shakers at 37° C. in standard LB-medium. *Agrobacterium tumefaciens* strains are grown at 28° C. in MinA medium supplemented with 0.1% glucose [Ausubel et al., (1987). Current Protocols in Molecular Biology, Green Publishing Associates and Wiley Inter-sciences, New York, Chichester, Brisbane, Toronto, and Singapore].

In all cloning procedures the *E. coli* strain JM83, (F$^-$, Δ(lac-pro), ara, rpsL, φ80, dlacZM15) is used as the preferred recipient for recombinant plasmids.

Binary vectors are conjugated to *Agrobacterium tumefaciens* strain LBA 4404, a strain containing the Ti-plasmid vir region, [Hoekema et al (1983). Nature 303: 179] in standard triparental matings using the *E. coli* HB101, containing the plasmid pRK2013 as a helper strain. [Figurski and Helinski, (1979). Proc. Natl. Acad. Sci. U.S.A. 76: 1648]. Appropriate *Agrobacterium tumefaciens* recipients are selected on media containing rifampicin (50 μg/ml) and kanamycine (50 μg/ml).

Cloning of fragments in the vectors pUC19 [Yanish-Perron et al (1985). Gene 33: 103], pBluescript (Stratagene), pBIN19 [Bevan et al (1984). Nucl. Acids Res. 12: 8711] or derivatives, restriction enzyme analysis of DNA, transformation to *E. coli* recipient strains, isolation of plasmid DNA on small as well as large scale, nick-translation, in vitro transcription, DNA sequencing, Southern blotting and DNA gel electrophoresis are performed according to standard procedures [Maniatis et al (1982).

Molecular Cloning: A Laboratory Manual. Cold Spring Harbor Laboratory, New York; Ausubel et al supra, (1987)].

DNA amplification using the polymerase chain reaction (PCR) was performed as recommended by the supplier of the Taq polymerase (Perkin Elmer Cetus). Amplification of RNA by reverse transcription and subsequent standard DNA amplification was performed using the Gene Amp RNA PCR as recommended by the supplier (Perkin Elmer Cetus).

Example 1
Isolation of CMV particles and genetic material therein

A CMV serogroup I is isolated from squash and maintained on squash by mechanical passaging. Virus is purified from systemically infected squash leaves essentially following the procedure according to Francki et al [(1979) CMI/AAB Descr. of Plant Viruses 213]. Approximately 100 μg of virus in a volume of 250 μl is extracted with phenol, then with a mixture of phenol and chloroform and finally with chloroform. RNA is precipitated with ethanol and collected by centrifugation. The pellet is dissolved in 20 μl of water.

Example 2
Isolation of ToMV particles and genetic material therein

A ToMV isolate from tomato, is maintained on tobacco via mechanical passaging. Virus is purified from systemically infected tobacco leaves essentially following the method essentailly according to Hollings & Huttinga [(1976) CMI/AAB Descr. of Plant Viruses 156]. Approximately 200 μg of virus in a volume of 300 μl is extracted with phenol, then with a mixture of phenol and chloroform and finally with chloroform. The RNA is precipitated with ethanol and collected by centrifugation. The pellet is dissolved in 50 μl of water.

Example 3
Molecular cloning of CMV RNA 3

The sequence of RNA 3 of CMV is isolated using RNA-based PCR on purified CMV RNA (Perkin Elmer Cetus supra). Two primers are designed, ZUP069:

(5' TTTGGATCCA CGTGGTCTCC TTTTGGAG 3'), which is complementary to the first 16 nucleotides at the 3' end of RNA 3 of CMV (Seq. Id No.1), and ZUP068:

(5' TTTGGATCCG TAATCTTACC ACT 3')
which is identical to the first 14 nucleotides at the 5' end of RNA 3 of CMV (Seq. Id. No.1). Both primers contain BamH1 restriction sites to enable further cloning of the amplified DNA molecules. Purified CMV RNA is subjected to the Gene Amp RNA PCR, and the resulting PCR fragment is isolated from an agarose gel and cloned into Sma1-linearized pUC19, yielding the recombinant plasmid pZU181.

Example 4
Molecular cloning of TSWV S RNA

A cDNA clone containing almost the complete TSWV S RNA-specific sequence was constructed by fusion of cDNA clones 520 and 614 on the unique EcoR1 site yielding pTSWV-S1 [De Haan et al (1990). J. Gen. Virol. 71: 1001]. The complete sequence of TSWV S RNA is isolated using RNA-based PCR on purified pTSWV-S1 DNA (Perkin Elmer Cetus supra). Two primers are designed, ZUP250:

5' (TTTGGATCCA GAGCAATCGT GTCAATTTTG TGTTCATACC TTAAC) 3' which comprises 36 nucleotides identical to the first 36 nucleotides at the 5' end of TSWV S RNA (Seq. Id. No.8), and ZUP251:

```
5' TTTCCATGGC ATGCGACTAC ACTTGCGGTT CTAACTGCTA CTCTTCTTCA

GACGTTTCTA CTGCTCAAGC TGCCGGATAT AAACTTCACG AAGACGGTGA

AACTGTTGGA TCTAATTCTT ACCCACACAA ATACAACAAC TACGAAGGTT

TTGATTTCTC TGTGAGCTCT CCCTAC 3'
```

5' (TTTGGATCCA GAGCAATTGT GTCAGAATTT TGTTCATAAT CAAACCTCAC TT) 3'

```
5' GGGCCATGGT TATGTACATT CAACGAAGTT GTTACCAGAA GCACCAGTGT

GAGTGATAAC ACCAGCATGT TGGTTGTTTT CGTTGAAGAC GACACGGTCA

GCACCTGGAG AAGGACCAGA GTAAACATCA CCGCTAGAGA GGATAGGCCA

TTCGTAGTAG GGAGAGCTCA C 3'
``` which comprises 43 nucleotides complimentary to the first 43 nucleotides at the 3' end of TSWV S RNA (Seq. Id. No.8). Both primers contain BamHI restriction sites to enable further cloning of the amplified DNA molecules. The resulting PCR fragment is isolated from an agarose gel and cloned into Sma1-linearized pUC19, yielding the recombinant plasmid pTSWV-S2.

Example 5
Molecular cloning of the CP and P30 genes of ToMV

The sequence of the genes corresponding to the coat protein (CP) and P30 of ToMV is isolated using RNA-based PCR. Primer ZUP112 spans either side of the translational start codon of the CP gene of ToMV RNA:

5' GTATTAACCA TGGCTTACTC 3' (comprising 13 nucleotides identical to nucleotides 121–133 of Seq. Id. No.1) and primer ZUP113 spans either side of the translational stop codon of the CP gene of ToMV RNA:

5' GCACCCATGG ATTAAGATG 3' (comprising 16 nucleotides complementary to nucleotides 595–610 of Seq. Id. No.1), and primer ZUP117 spans either side of the translational start codon of the P30 gene of ToMV RNA:

5' TATTTCTCCA TGGCTCTAGT 3' (comprising 13 nucleotides identical to nucleotides 121–133 of Seq. Id No.6), and primer ZUP118 spans either side of the translational stop codon of the P30 gene of ToMV RNA:

5' GAGTAAGCCA TGGTTAATAC 3' (comprising 13 nucleotides complementary to nucleotides 911–923 of Seq. Id. No.6)

The primers contain Nco1 restriction sites to enable further cloning of the amplified DNA molecules. Purified ToMV RNA is subjected to the Gene Amp RNA PCR. Resulting PCR fragments are isolated from an agarose gel and cloned into Sma1-linearized pUC19, yielding the recombinant plasmids pZU183 (containing the CP gene) and pZU206 (containing the P30 gene).

Example 6
Synthesis of the ribonuclease T1 gene

The sequence of the gene corresponding with ribonuclease T1 is synthesized on a commercial DNA synthesizer (Pharmacia LKB, Gene assembler plus) as primer ZUP110 (comprising nucleotides identical to nucleotides 121–293 of Seq. Id No.4):

and primer ZUP111 (comprising nucleotides complementary to nucleotides 278–446 of Seq. Id. No.4):

Both primers contain Nco1 restriction sites to enable further cloning of the amplified DNA molecules. The primers are annealed and subjected to a standard DNA PCR. The amplified DNA fragment is isolated from an agarose gel and cloned into Sma1-linearized pUC19, yielding the recombinant plasmid pZU230.

Example 7
Construction of an expression vector pZU-A

The 35S cauliflower mosaic virus (CaMV) promoter fragment is isolated from the recombinant plasmid pZO27, a derivative of pUC19 carrying as a 444 bp HindIII-PstI fragment the HincII-HphI region of the 35S promoter of CaMV strain Cabb-S [Franck et al (1980). Cell 21: 285–294]. The nucleotide sequences of CaMV strains are very similar for the different strains. The 35S promoter fragment is excised from pZO27 as a 472 bp EcoRI-PstI fragment which contains: a part of the polylinker region, 437 bp of the non-transcribed region and the transcription initiation site and 7 bp of the non-translated leader region but not containing any 35S translational initiators. The 35S promoter fragment is ligated using T4 ligase into EcoRI-PstI linearized pZO008. The plasmid pZO008 carries the nopaline synthase (NOS) polyadenylation signal as a 270 bp PstI-HindIII fragment. The resulting recombinant plasmid pZU-A carries the 35S promoter, a unique PstI site and the NOS terminator [Gielen et al (1991) Bio/Technology 10:1363].

Example 8

Construction of a plant transformation vector, which yields a transcript which replicates upon infection with CMV The 5' end of the minus-sense RNA 3 of CMV is fused directly to the transcription initiation site of the CaMV 35S promoter using two primers ZUP148:

5' CCACGTCTTC AAAGCAAG 3' (complementary to nucleotides of the CaMV 35S promoter), and primer ZUP146:

5' CTTCGCACCT TCGTGGGGGC TCCAAAAGGA GACCACCTCT CCAAATGAAA 3' (comprising nucleotides complementary to nucleotides 1860–1827 of Seq. Id. No.1)

with pZU-A as a template in a standard DNA PCR reaction. The amplified DNA fragment is digested with EcoRV and cloned in EcoRV linearized pZU-A. The resulting plasmid is digested with BstX1 and Pst1 and purified on an agarose gel. pZU181 is digested with Pst1 and BstX1, the 2.1 kb insert DNA is purified on an agarose gel and subsequently cloned into the gel-purified pZU-A derivative, yielding pCMV3AS-1.

The movement protein (MP) coding domain of pCMV3AS-1 is replaced by a unique Nco1 cloning site and the axehead structure of the Hepatitis delta viral RNA is cloned downstream of the 3' end of the minus-sense RNA 3 of CMV, by PCR amplification of two DNA fragments using pCMV3AS-1 as a template. The first DNA fragment is amplified using primers ZUP050:

5' AGCTGCTAAC GTCTTATTAA G 3' (comprising nucleotides complementary to nucleotides 1020–1039 of Seq. Id. No.1)

and ZUP329:

5' GTCTTTAGCA CCATGGTG 3' (comprising nucleotides identical to nucleotides 604–612 of Seq Id. No.1)

The DNA fragment is digested with Nru1 and Nco1 and a 411 bp long DNA fragment (position 607–1016 Seq. Id. No.1) is isolated from an agarose gel. The second DNA fragment is amplified using primers ZUP327:

5' GGAGAGCCAT GGCTCGGG 3' (comprising nucleotides complementary to nucleotides 115–126 of Seq. Id. No.1)

and ZUP350, a primer synthesised with nucleotides comprising nucleotides complementary to antigenomic hepatitis delta virus RNA as described by Perrotta A. T. & Been M. D. (1991) Nature Vol 350(4) pp434–436 ligated to nucleotides identical to nucleotides 1–14 (3' end of the primer) of Seq. Id. No. 1:

pCMV3AS-2 derived plasmids are digested with HindIII and the DNA fragments containing the chimaeric genes are isolated from an agarose gel and ligated into HindIII linearized pBIN19, resulting in binary plant transformation vectors pBINCMV3-CP, pBINCMV3-P30 and pBINCMV3-T1 respectively.

Example 9

Construction of a plant transformation vector, which yields a transcript which replicates upon infection with TSWV The 5' end of the minus-sense TSWV S RNA is fused directly to the transcription initiation site of the CaMV 35S promoter using two primers ZUP148 (Example 8), and primer ZUP255:

5' ACACAATTGC TCTCCTCTCC AAATGAAA 3' (comprising nucleotides identical to nucleotides 2608–2621 of Seq. Id. No.8)

with pZU-A as a template in a standard DNA PCR reaction. The amplified DNA fragment is digested with EcoRV and cloned in EcoR5 linearized pZU-A. The resulting plasmid is digested with Mun1 and Pst1 and purified on an agarose gel. pTSWV-S2 is digested with Pst1 and Mun1, the 2.9 kb insert DNA is purified on an agarose gel and subsequently cloned into the gel-purified pZU-A derivative, yielding pTSWVSAS-1.

The N coding domain of pTSWVSAS-1 is replaced by a unique Nco1 cloning site and the axehead structure of the Hepatitis delta viral RNA is cloned downstream of the 3' end of the minus-sense TSWV S RNA, by PCR amplification of two DNA fragments using pTSWVSAS-1 as a template. The first DNA fragment is amplified using primers ZUP252:

5' GACCCGAAAG GGACCAATTT C 3' (comprising nucleotides complimentary to nucleotides 911–930 of Seq Id. No.8)

and ZUP253:

5' TTTCCATGGC TGTAAGTTAA ATT 3' (comprising nucleotides identical to nucleotides 636–655 of Seq Id. No.8)

The DNA fragment is digested with Ba11 and Nco1 and a 269 bp long DNA fragment (position 636–911 Sequence Id No.8) is isolated from an agarose gel. The second DNA fragment is amplified using primers ZUP254:

5' TTTCCATGGT GATCGTAAAA G 3' (comprising nucleotides complementary to nucleotides 140–157 of Seq. Id No.8)-

5'TTTCTGCAGA TCTTAGCCAT CCGAGTGGA CGTGCGTCCT CCTTCGGATG

CCCAGGTCGG ACCGCGAGGA GGTGGAGATG CCATGCCGAC CCGTAATCTT

ACCACT)3'.

The DNA fragment is digested with Pst1 and Nco1 and a 208 bp. long DNA fragment is isolated from an agarose gel. Both isolated DNA fragments are cloned in pCMV3AS-1, linearized with Pst1 and Nru1, to yield pCMV3AS-2. Genes coding for elicitors (example 5) or cell inhibitory proteins (example 6) can be cloned as Nco1 DNA fragments into the unique Nco1 site of pCMV3AS-2. The resulting and ZUP255 a primer synthesised with nucleotides comprising nucleotides complementary to antigenomic hepatitis delta virus RNA as described by Perrotta A. T. & Been M. D. (1991) Nature Vol 350(4) pp434–436, ligated to nucleotides identical to nucleotides 1–14 (3' end of the primer) of Seq. Id. No. 8:

```
5' TTTCTGCAGA TCTTAGCCAT CCGAGTGGAC GTGCGTCCTC CTTCGGATGC

CCAGGTCGGA CCGCGAGGAG GTGGAGATGC CATGCCGACC CAGAGCAATC

GTGTC 3'
```

The DNA fragment is digested with Pst1 and Nco1 and a 245 bp. long DNA fragment is isolated from an agarose gel. Both isolated DNA fragments are cloned in pTSWVSAS-1, linearized with Pst1 and Ba11, to yield pTSWVSAS-2. Genes coding for elicitors (example 5) or cell inhibitory proteins (example 6) are cloned as Nco1 DNA fragments into the unique Nco1 site of pTSWVSAS-2. The resulting pTSWVSAS-2 derived plasmids are digested with Xba1 and the DNA fragments containing the chimaeric genes are isolated from an agarose gel and ligated into Xba1 linearized pBIN19, resulting in binary plant transformation vectors pBINTSWVS-CP (Seq Id No.8), pBINTSWVS-P30 and pBINTSWVS-T1 respectively.

Example 10
Selection of suitable host plants
1) Tobacco, Nicotiana tabacum var. Samsun EN. A tobacco cultivar harboring the N' gene of N. sylvestris showing an HS response upon infection with ToMV. The CP of ToMV elicits a strong HSR defense reaction in this host.
2) Tomato, Lycopersicon esculentum var. ATV847, parental line for commercial hybrids Yaiza and Gemma. A tomato line harboring the Tm-$2^2$ resistance gene to ToMV. It has been demonstrated that the P30 of ToMV elicits a HS response in this resistag30 nt genotype [Fraser (1986) CRC Crit. Rev. Plant Sci.3: 257; Keen (1990). Ann. Rev. Genet. 24: 447].

Example 11
Transformation of binary vectors to tobacco and tomato plant material
Methods to transfer binary vectors to plant material are well established and known to a person skilled in the art. Variations in procedures exist due to for instance differences in used Agrobacterium strains, different sources of explant material, differences in regeneration systems depending on as well the cultivar as the plant species used.

The binary plant transformation vectors as described above are used in plant transformation experiments according to the following procedures. Binary vector constructs are transferred by tri-parental mating to an acceptor *Agrobacterium tumefaciens* strain, followed by southern analysis of the ex-conjugants for verification of proper transfer of the construct to the acceptor strain, inoculation and cocultivation of axenic explant material with the *Agrobacterium tumefaciens* strain of choice, selective killing of the *Agrobacterium tumefaciens* strain used with appropriate antibiotics, selection of transformed cells by growing on selective media containing kanamycine, transfer of tissue to shoot-inducing media, transfer of selected shoots to root inducing media, transfer of plantlets to soil, assaying for intactness of the construct by southern analyses of isolated total DNA from the transgenic plant, assaying for proper function of the inserted chimaeric gene by northern analysis and/or enzyme assays and western blot analysis of proteins [Ausubel et al supra, (1987)].

Example 12
Expression of chimaeric sequences in tobacco and tomato plant cells
RNA is extracted from leaves of regenerated plants using the following protocol. Grind 200 mg leaf material to a fine powder in liquid nitrogen. Add 800 µl RNA extraction buffer (100 mM Tris-HCl (pH 8,0), 500 mM NaCl, 2 mM EDTA, 200 mM 62-Mercaptoethanol, 0,4% SDS) and extract the homogenate with phenol, collect the nucleic acids by alcohol precipitation. Re suspend the nucleic acids in 0,5 ml 10 mM Tris-HCl (pH 8,0), 1 mM EDTA, add LiCl to a final concentration of 2M, leave on ice for maximally 4 hours and collect the RNA by centrifugation. Re suspend in 400 µl 10 mM Tris-HCl (pH 8,0), 1 mM EDTA and precipitate with alcohol, finally re-suspend in 50 µl 10 mM Tris-HCl (pH 8,0), 1 mM EDTA. RNAs are separated on glyoxal/agarose gels and blotted to Genescreen as described by van Grinsven et al [(1986). Theor. Appl. Gen. 73:94–101]. Recombinant viral RNA sequences are detected using DNA or RNA probes labeled with [$^{32}$P], [$^{35}$S] or by using non-radioactive labeling techniques. Based on northern analysis, it is determined to what extent the regenerated plants express the chimaeric recombinant viral genes.

Plants transformed with recombinant viral DNA sequences are also subjected to western blot analysis after inoculation with the respective virus. Proteins are extracted from leaves of transformed plants by grinding in sample buffer according to Laemmli [(1970). Nature 244: 29]. A 50 µg portion of protein is subjected to electrophoresis in a 12,5% SDS-polyacrylamide gel essentially as described by Laemmli supra, (1970). Separated proteins are transferred to nitrocellulose electrophoretically as described by Towbin et al [(1979). Proc. Natl. Acad. Sci. U.S.A. 76: 4350]. Transferred proteins are reacted with antiserum raised against purified ToMV particles or against purified P30 protein, according to Towbin et al supra, (1979). Based on the results of the western analysis, it is determined that transformed plants do express elicitor proteins after inoculation with the respective virus.

Example 13
Resistance of tobacco and tomato plants against CMV or TSWV infection
Transformed plants are grown in the greenhouse under standard quarantine conditions in order to prevent any infections by pathogens. The transformants are self-pollinated and the seeds harvested. Progeny plants are analyzed for segregation of the inserted gene and subsequently infected with CMV or TSWV by mechanical inoculation. Tissue from plants systemically infected with CMV or TSWV is ground in 5 volumes of ice-cold inoculation buffer (10 mM phosphate buffer) and rubbed in the presence of carborundum powder on the first two fully extended leafs of approximately 5 weeks old seedlings. Inoculated plants are monitored for symptom development during 3 weeks after inoculation.

Plants containing CMV Related DNA Sequences or TSWV related DNA sequences show reduced susceptibility to CMV or TSWV infection compared with untransformed control plants which show severe systemic CMV or TSWV symptoms within 7 days after inoculation.

I claim:

1. A DNA construct comprising: a sequence coding for a minus sense RNA, wherein said sequence has a complement which hybridizes to a sequence selected from the group consisting of SEQ ID NO: 1, SEQ ID NO:4, SEQ ID NO:6, and SEQ ID NO:8 under hybridization conditions involving incubation in a buffer system for about 16 hours at 55° C. and washing 3× in a buffer comprising 0.1×SSC and 0.1% SDS at 65° C. for approximately an hour each time; a promoters; and a terminator, wherein said construct is under expression control of the promoter and terminator and said minus sense RNA is replicated in a plant cell by a viral RNA dependent RNA polymerase upon viral infection and leads to the production of at least one protein or peptide.

2. The construct of claim 1, wherein said sequence has a complement which hybridizes to SEQ ID NO:1 under hybridization conditions involving incubation in a buffer system for about 16 hours at 55° C. and washing 3× in a buffer comprising 0.1×SSC and 0.1% SDS at 65° C. for approximately an hour each time.

3. The construct of claim 1, wherein said sequence has a complement which hybridizes to SEQ ID NO:4 under hybridization conditions involving incubation in a buffer system for about 16 hours at 55° C. and washing 3× in a buffer comprising 0.1×SSC and 0.1% SDS at 65° C. for approximately an hour each time.

4. The construct of claim 1, wherein said sequence has a complement which hybridize to SEQ ID NO:6 under hybridization conditions involving incubation in a buffer system for about 16 hours at 55° C. and washing 3× in a buffer comprising 0.1×SSC and 0.1% SDS at 65° C. for approximately an hour each time.

5. The construct of claim 1, wherein said sequence has a complement which hybridizes to SEQ ID NO:8 under hybridization conditions involving incubation in a buffer system for about 16 hours at 55° C. and washing 3× in a buffer comprising 0.1×SSC and 0.1% SDS at 65° C. for approximately an hour each time.

6. The construct of claim 1 wherein said protein elicits a hypersensitive response.

7. The construct of claim 1 wherein the protein is selected from the group consisting of plant virus, bacterial, fungal and nematode originating proteins.

8. The construct of claim 1 wherein the protein is selected from the group consisting of ribonucleases, proteinases, ribosomal inhibitory proteins and cell wall degrading proteins.

9. The construct of claim 1 wherein the promoter is a constitutive promoter selected from the group consisting of viral, fungal, bacterial and plant derived promoters.

10. The construct of claim 9 wherein the promoter is a CaMV 19S, CaMV 35S, nopaline synthase, octopine synthase, or heat shock 80 promoter.

11. Plants containing in their genome the construct of claim 1.

12. A process of preparing virus resistant plants comprising the steps of,
   a) inserting into the genome of a plant cell a DNA construct which comprises a sequence coding for a minus sense RNA, a promoter, and a terminator wherein said sequence coding for a minus sense RNA has a complement which hybridizes to a sequence selected from the group consisting of SEQ ID NO:1, SEQ ID NO:4, SEQ ID NO:6, and SEQ ID NO:8 under hybridization conditions involving incubation in a buffer system for about 16 hours at 55° C. and washing 3×in a buffer comprising 0.1× SSC and 0.1% SDS at 65° C. for approximately an hour each time, and wherein said construct is under expression control of the promoter and terminator, the minus sense RNA includes the genome or part of the genome of a plant virus, and said minus sense RNA is replicated in a plant cell by a viral RNA dependent RNA polymerase upon viral infection;

b) obtaining tranformed cells; and c) regenerating from the transformed cells genetically transformed plants
wherein said transformed plants contain in their genome said DNA construct and are virus resistant.

13. The transformed virus resistant plants obtained according to claim 12.

14. The transformed plants of claim 13 wherein the transformed plants are resistant to plant viruses selected from the group consisting of potyviruses, potexviruses, tobamoviruses, luteoviruses, cucumoviruses, bromoviruses and tospoviruses.

15. The progeny of the transformed plants of claim 13 wherein said progeny contain in their genome said DNA construct and are virus resistant.

16. The transformed plants of claim 13 wherein the plants are resistant to CMV or TSWV viral infection.

17. A DNA construct comprising (a) a sequence selected from the group consisting of SEQ ID No. 1, SEQ ID No.4, SEQ ID No.6 and SEQ ID No.8, which encodes a minus sense RNA, (b) a promoter, and (c) a terminator wherein said promoter and terminator function in plants and the minus sense RNA is replicated in a plant cell by a viral RNA dependent RNA polymerase upon viral infection and produces at least one protein or peptide.

18. The construct of claim 17 wherein the protein is selected from the group consisting of ribonucleases, proteinases, ribosomal inhibitory proteins and cell wall degrading proteins.

19. The construct of claim 17 wherein the construct comprises a constitutive promoter selected from the group consisting of viral, fungal, bacterial and plant derived promoters.

20. The construct of claim 18 wherein the promoter is a CaMV 19S, CaMV 35S, nopaline synthase, octopine synthase, or heat shock 80 promoter.

21. Plants containing in their genome a construct according to claim 17.

22. A process of preparing virus resistant plants comprising the steps of:

a) inserting into the genome of a plant cell a DNA construct of claim 17;

b) obtaining transformed plant cells; and c) regenerating from the transformed plant cells genetically transformed plants wherein said plants include in their genome the DNA construct of claim 17 and the plants are virus resistant.

23. The construct of claim 17, wherein said minus sense RNA is encoded by SEQ ID No.1.

24. The construct of claim 17, wherein said minus sense RNA is encoded by SEQ ID No.4.

25. The construct of claim 17, wherein said minus sense RNA is encoded by SEQ ID No.6.

26. The construct of claim 17, wherein said minus sense RNA is encoded by SEQ ID No.8.

* * * * *